US008156853B2

(12) United States Patent
Fujiwara et al.

(10) Patent No.: US 8,156,853 B2
(45) Date of Patent: Apr. 17, 2012

(54) AUTOMATIC THIN-SECTION MANUFACTURING SYSTEM

(75) Inventors: Hirohito Fujiwara, Chiba (JP); Tetsumasa Ito, Chiba (JP); Koji Fujimoto, Chiba (JP); Tatsuya Miyatani, Chiba (JP)

(73) Assignee: Seiko Instruments, Inc., Chiba (JP)

( * ) Notice: Subject to any disclaimer, the term of this patent is extended or adjusted under 35 U.S.C. 154(b) by 549 days.

(21) Appl. No.: 12/033,474

(22) Filed: Feb. 19, 2008

(65) Prior Publication Data

US 2008/0202308 A1    Aug. 28, 2008

(30) Foreign Application Priority Data

Feb. 27, 2007   (JP) ................. 2007-047445

(51) Int. Cl.
*B26D 7/26* (2006.01)
*B26D 7/06* (2006.01)
*B23D 19/00* (2006.01)

(52) U.S. Cl. ...................... 83/703; 83/698.21
(58) Field of Classification Search .............. 83/703, 83/915.5, 78, 698.21; 483/16, 58; *B23Q 3/157, B23Q 3/155*
See application file for complete search history.

(56) References Cited

U.S. PATENT DOCUMENTS

| | | | | |
|---|---|---|---|---|
| 3,273,879 A | * | 9/1966 | Floren | 269/61 |
| 3,832,923 A | * | 9/1974 | Lassmann et al. | 83/16 |
| 4,207,790 A | * | 6/1980 | Endo | 83/699.11 |
| 4,766,465 A | * | 8/1988 | Takahashi | 355/53 |
| 5,461,953 A | * | 10/1995 | McCormick | 83/36 |
| 5,752,425 A | * | 5/1998 | Asakura et al. | 83/713 |
| 5,906,148 A | * | 5/1999 | Aihara et al. | 83/72 |
| 6,644,162 B1 | * | 11/2003 | Temple et al. | 83/703 |
| 2003/0022271 A1 | * | 1/2003 | Voneiff et al. | 435/40.52 |
| 2003/0215936 A1 | * | 11/2003 | Kallioniemi et al. | 435/287.1 |
| 2006/0272467 A1 | * | 12/2006 | Hendrick et al. | 83/730 |
| 2007/0141711 A1 | * | 6/2007 | Stephens et al. | 436/43 |

FOREIGN PATENT DOCUMENTS

| | | |
|---|---|---|
| JP | 54-079098 A | 6/1979 |
| JP | 10-090132 A | 4/1998 |
| JP | 2001-289747 A | 10/2001 |
| JP | 2003-532109 A | 10/2003 |
| JP | 2004-28910 A | 1/2004 |

OTHER PUBLICATIONS

Office Action from counterpart Japanese Application No. 2007-047445, dated Sep. 20, 2011, 2 pages.

* cited by examiner

*Primary Examiner* — Ghassem Alie
*Assistant Examiner* — Bharat C Patel
(74) *Attorney, Agent, or Firm* — Brinks Hofer Gilson & Lione

(57) ABSTRACT

A manufacturing system for producing thin sections of a biological sample embedded in a block. The system includes, a blade holder disposed at a rake angle relative to the block, a mounting plane on which a plurality of cutting blades are mounted, an adsorptive member on the mounting plane that maintains the posture of the cutting blades, a pressing member that presses a selected cutting blade against the mounting plane, a conveyor unit that slides out the cutting blades by sequentially conveying the plurality of cutting blades to feed them one by one on the mounting plane, a transportation unit that moves the block relative to the holder, such that the cutting blade cuts out a thin section from the sample, and a control unit that operates the conveyor unit to exchange the selected cutting blade.

5 Claims, 18 Drawing Sheets

AUTOMATIC THIN-SECTION MANUFACTURING SYSTEM

This application claims priority under 35 U.S.C. §119 to Japanese Patent Application No JP2007-047445 filed Feb. 27, 2007, the entire content of which is hereby incorporated by reference.

BACKGROUND OF THE INVENTION

1. Field of the Invention

The present invention relates to an automatic thin-section manufacturing system which manufactures thin sections by thinly cutting an embedded block containing embedded therein a biological sample.

2. Background Art

Conventionally, a microtome has been known in general as a tool to use in preparing thin section slide samples for physicochemical experiments and microscopic observations. The thin section slides are prepared by fixing thin sections about several micrometers (for instance, from 3 µm to 5 µm) in thickness on a substrate such as a glass slide. A generally employed method for preparing a thin section sample using a microtome is described below.

An embedded block is prepared by first subjecting a formalin-fixed biological sample taken out from living bodies, laboratory animals, and the like to paraffin substitution, and then solidifying the periphery thereof with paraffin to prepare a solid block. Then, preliminary cutting is carried out by setting the embedded block in a microtome, i.e., a thin sectioning apparatus especially designed for this purpose. By preliminary cutting, the surface of the embedded block is smoothed, and the biological sample, which is intended to be subjected to the experiment or observation, is brought into a state that is exposed to the surface.

Main cutting is carried out upon completion of preliminary cutting. In this process step, the cutting blade of the microtome slices the embedded block to provide ultra-thin sections at the predetermined thickness. Thin sections can be obtained in this manner. In such a case, more accurate observation data can be made available by slicing the embedded block as thin as possible, since the thickness of the thin section can be brought near to that of a living cell. Accordingly, it is required to manufacture thin sections as thin as possible.

After the main cutting, thin sections thus obtained are flattened in the flattening process. More specifically, because the thin sections obtained by the main cutting are sliced so thin, they are apt to be wrinkled or curled (U-shaped). Thus, flattening step is necessary to remove the wrinkles or curls from the thin sections.

In general, flattening is performed by using water and hot water. Firstly, the thin section obtained by main cutting is released in water to set afloat. In this manner, large wrinkles or curls of the thin section can be removed while preventing the paraffin, which contains embedded therein the biological sample, from sticking to each other. The thin section is then floated in hot water. The remaining wrinkles and curls can be thus removed from the thin section, because the thin sections are more easily extended in hot water.

After finishing hot flattening, the thin section is mounted on a substrate by scooping it onto a substrate such as a slide glass. If flattening is insufficient at this point, the substrate having the thin section mounted thereon is wholly placed on a hot plate and the like to further apply heat. In this manner, the thin section can be further flattened.

Finally, the substrate having mounted thereon the thin section is dried by placing it inside an oven. By drying, the water adhered to the thin section during flattening evaporates, and the thin section is fixed on the substrate. As a result, a thin section slide sample can be obtained.

Since most of the manufacturing processes described hereinbefore require highly skilled technique and experience, in general, the process is committed to a manual operation of a skillful technician. Recently, however, in order to reduce the load of the operator, a section-slides manufacturing apparatus which automatically carries out a part of the process is provided (see, for example, JP-A-2004-28910).

The section-slides manufacturing apparatus automatically operates the process of preparing thin section slide samples by cutting an embedded block set in the apparatus, transporting the thus prepared thin section on a carrier tape to transfer the thin section on a slide glass, and flattening the thin section by entirely transferring the slide glass having thereon the thin section to the flattening apparatus. The burden of the operator can be somewhat reduced by using the section-slides manufacturing apparatus.

However, the section-slides manufacturing apparatus described in the JP-A-2004-28910 above still had the following problems to be solved.

Firstly, in order to manufacture high quality thin section sample slides by thinly cutting the embedded block to manufacture the thin sections, the thin sections should be sectioned at a predetermined thickness and with the cutting face as flat and clean as possible. Accordingly, the operators must be particularly aware of not only the cutting speed and the like, but also the edge of the cutting blade. If thin cutting should be carried out with a blunt-edged cutting blade, difficulties were found in thinly cutting the embedded block into thin sections of desired thickness (for instance, from 3 µm to 5 µm). Furthermore, there were possibilities of breaking the thin sections in some cases. Moreover, there was a possibility of applying too high a load to compress (deform) the thin section, thereby making it unfeasible to recover (flatten) in the subsequent flattening process step. Thus, in order to avoid such inconveniences, the operator must routinely exchange the cutting blades.

However, since a large number of embedded blocks must be processed, and because plural thin sections are cut out from a single embedded block, the cutting blades had to be frequently exchanged. In particular, generally in case of main sectioning, the cutting blade was changed to a new one because a sharp edge was necessary. Accordingly, the operator had to bear great burden.

It is possible to somewhat shift the load from the operators by using the apparatus described in the JP-A-2004-28910; yet, however, the operator had to exchange the cutting blades. Thus, the operators were still hard-pressed, and the apparatus was not easy for handling.

Furthermore, the cutting blade is generally set at a predetermined rake angle. Thus, in case of exchanging the cutting blade, the cutting blade must be kept supported, or it slides down by the gravity and cannot be set at the regular position. Thus, the operator had to hold the cutting blade carefully lest it should slide off during the exchange operation. This laid additional burden on the operator.

The present invention has been accomplished under such circumstances with an objective to provide an automatic thin-section manufacturing system capable of manufacturing thin sections by thinly cutting an embedded block while automatically exchanging the cutting blades disposed at such a state that the predetermined rake angle is maintained, thereby minimizing the burden of the operator.

SUMMARY OF THE INVENTION

In order to solve the problems above, the present invention provides the following solutions.

According to an aspect of the invention, there is provided an automatic thin-section manufacturing system for manufacturing thin sections by thinly cutting out an embedded block having embedded therein a biological sample while setting said embedded block at a predetermined rake angle, said system comprising: a long cutting blade having a cutting edge on one end; a holder disposed in such a manner that it makes the rake angle with respect to the surface of the embedded block; a mounting plane provided to the front end of the holder, on which plural cutting blades are mounted and aligned with their cutting edges exposed to the outer side; an adsorptive member provided along the mounting plane, which maintains the posture of the cutting blades by adsorbing the base end side of the cutting blades mounted on the mounting plane; a first pressing member provided to the holder, which presses, among the plural cutting blades that are mounted and aligned on the mounting plane, the cutting blade allocated to the predetermined position against the mounting plane; a conveyor unit which slides out the cutting blades that are linearly aligned on the mounting plane, by sequentially conveying the plural cutting blades to feed them one by one on the mounting plane; a transportation unit which moves the embedded block relative to the holder, such that the cutting blade pressed by the first pressing member cuts out the thin section from the embedded block; and a control unit which, after performing thin sectioning for a predetermined time, exchanging the cutting blade used for the thin sectioning by operating the conveyor unit to slide out the cutting blades.

In the automatic thin-section manufacturing system according to the invention, the conveyor unit first conveys the cutting blades one by one onto the mounting plane of the holder. Then, the first fed cutting blade is pushed by the next fed cutting blade to slide out along the mounting plane. In this manner, the cutting blades slide out in a line along the mounting plane. In this instance, the cutting blades are in such a state that their cutting edges are exposed to the outer side. Then, once the cutting blade that had slid out settles at the predetermined position of the mounting plane, the cutting blade is firmly fixed by a first pressing member which presses it against the mounting plane. In this manner, the pressed cutting blade is utilized as the cutting blade for sectioning.

After the cutting blade is fixed, a transportation unit moves the embedded block relative to the holder in order to thinly cut the embedded block with the press-fixed cutting blade. In this manner, thin sections are manufactured by cutting them out from the embedded block. Furthermore, because the holder is provided at a predetermined rake angle with respect to the surface of the embedded block, the cutting blade is provided similarly at the rake angle. Thus, sectioning can be smoothly performed at the predetermined rake angle. Further, after sectioning is completed for predetermined times, the control unit releases the pressing of the first pressing member, and, at the same time, operates the conveyor unit to convey a new cutting blade onto the mounting plane. In this manner, the used cutting blade remaining mounted on the mounting plane is pushed by the new cutting blade and slides out of the mounting plane. Then, when the new cutting blade comes to the predetermined position, the first pressing member presses the cutting blade to provide the cutting blade for sectioning. That is, the cutting blades are automatically exchanged every predetermined times of sectioning. Accordingly, the cutting blades are exchanged without involving any human power; hence, the burden on the operators can be minimized. Furthermore, high quality thin sections can be manufactured because sharp-edged cutting blades are provided constantly.

In particular, the base edge side (i.e., the side opposite to the cutting edge) of the cutting blades mounted on the mounting plane, inclusive of the one pressed by the first pressing member, is adsorbed by the adsorptive member. Hence, even if the holder should be tilted at the rake angle, the cutting blade remains free from the gravimetric force and does not slide down the mounting plane, but maintains the posture in a stable state. Accordingly, cutting blades can be smoothly exchanged while maintaining the rake angle.

Furthermore, in the case the cutting blade is pressed with the first pressing member, the amount of the cutting edge, which is protruded out from the holder and exposed to the outer side, can be maintained the same because the posture of the cutting blade is stably maintained. In this manner, the fluctuations of the cutting edges can be evened out, and hence, the embedded block can be sectioned under the same conditions even if the cutting blades are exchanged; thus, thin sections of same quality can be continuously manufactured.

According to another aspect of the invention, there is provided an automatic thin-section manufacturing system as the automatic thin-section manufacturing system above, wherein the adsorptive member is a plurality of magnets which adsorb the base end side of the cutting blade by a magnetic force.

In the automatic thin-section manufacturing system according to the invention, plural magnets are provided along the mounting plane, and the cutting blade is adsorbed by the magnetic force of the plurality of magnets. By using magnets, an adsorptive member can be realized by such a simple and low cost constitution which contribute in constructing a simplified and reduced cost constitution.

Furthermore, the automatic thin-section manufacturing system according to the invention is characterized in that the automatic thin-section manufacturing system above further comprises a second pressing member in the neighbor of the first pressing member, which again presses the cutting blade already used in the thin sectioning against the mounting plane, to reuse it as a cutting blade for preliminary cutting; and that the thin section is manufactured using the cutting blade which is pressed by the first pressing member after preliminarily cutting the embedded block with the cutting blade dedicated for preliminary cutting.

In the automatic thin-section manufacturing system according to the invention, the cutting blade that had been used for sectioning slides out from the predetermined position by the operation of the conveyor unit, and the second pressing member again presses the cutting blade against the mounting plane to firmly fix it. In this manner, the cutting blade once used for sectioning can be reused as a cutting blade for preliminary cutting. Thus, before starting sectioning of the embedded block, preliminary cutting is applied to the embedded block using the cutting blade pressed by the second pressing member allotted for preliminary cutting. Upon completion of preliminary cutting, sectioning is carried out using the cutting blade pressed by the first pressing member dedicated for the sectioning to obtain the thin section.

By reusing, instead of wasting, the cutting blades used for sectioning as the cutting blades for preliminary cutting, the cutting blades can be exchanged to use them effectively. Thus, the running cost can be suppressed.

According to a still other aspect of the invention, there is provided an automatic thin-section manufacturing system as described in one of the aspects above, wherein, the conveyor unit further comprises a storage case for storing the plural cutting blades; a conveyor path which is located between the storage case and the holder and having a conveyor plane tilted at the rake angle, such that the cutting blades are aligned and transported by making the conveyor plane flush with the mounting plane; and a conveyor mechanism which takes out the cutting blade one by one from the storage case, temporarily mounts it on the conveyor plane, and conveys the cutting blade along the conveyor plane to feed it on the mounting plane; provided that the adsorptive member is provided along the conveyor plane, such that it adsorbs the base end side of the cutting blade to maintain the posture of the cutting blade.

In the automatic thin-section manufacturing system according to the invention, on operating the conveyor unit, the conveyor mechanism conveys one cutting blade out from the storage case and temporarily mounts it on the conveyor plane of the conveyor path. Subsequently, the conveyor mechanism conveys the thus mounted cutting blade along the conveyor plane, and feeds it as it is onto the mounting plane of the holder. In particular, the conveyor path is provided at a state having the same rake angle as that of the holder, and the conveyor plane is leveled to the same flat of the mounting plane.

Accordingly, the cutting blade can be fed to the mounting plane already set at the rake angle. Thus, the cutting blade can be delivered smoothly to the holder.

Particularly, because an adsorptive member is provided along the conveyor plane, the cutting blade can stably retain its posture without sliding off and being influenced by gravitational force during delivery. Thus, the cutting blade already set at the rake angle can be surely fed to the mounting plane. Furthermore, because the cutting blade can be infallibly fed to the mounting plane of the holder via the conveyor path, the holder can be set freely at any position independent to the position of the storage case. Thus, this enables a design with higher degree of freedom.

In accordance with the invention, there is provided an automatic thin-section manufacturing system capable of manufacturing thin sections by thinly cutting an embedded block at an already set rake angle while automatically exchanging the cutting blades, thereby minimizing the burden of the operator by eliminating the cutting blade exchange operation which had been a burden to the operators. Furthermore, high quality thin sections can be manufactured because sharp-edged cutting blades are provided constantly for sectioning. Moreover, thin sections of the same quality can be continuously manufactured because the cutting blade can be exchanged while maintaining the cutting edge at the same amount of protrusion.

DETAILED DESCRIPTION OF THE PREFERRED EMBODIMENTS

Figure 1:
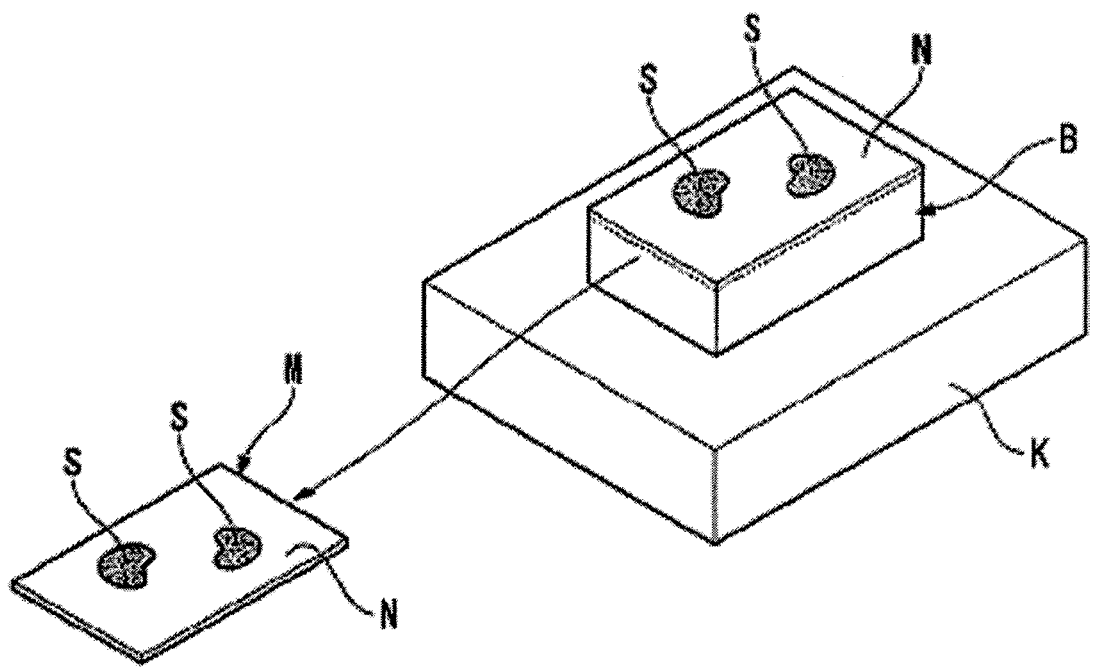
FIG. 1 is a perspective view showing a state in which an automatic thin-section manufacturing system according to the invention produces a thin section from an embedded block.

An embodiment of an automatic thin-section manufacturing system according to the invention is described below by making reference to FIGS. 1 to 19. Referring to FIG. 1, the automatic thin-section manufacturing system according to the invention is a system which thinly cuts an embedded block B comprising an embedding medium N having embedded therein a biological sample S (for instance, ultra-thin sections from 3 μm to 5 μm in thickness), at a preliminarily set rake angle θ, to manufacture a thin section M.

The embedded block B is prepared by paraffin-substituting the water contained in the formalin-fixed biological sample S, and then solidifying the surroundings with an embedding agent N such as paraffin and the like to obtain a block. Thus, at this moment, the biological sample S is obtained embedded in paraffin. As the biological sample S, for instance, there can be used a tissue of organs and such taken out from human bodies and laboratory animals and the like, which is properly selected depending on the fields, such as the medical, pharmaceutical, food, and biological fields. In the present embodiment, the description is made on a case the embedded block B is fixed in a cassette K formed in a box-like shape.

Figure 2:
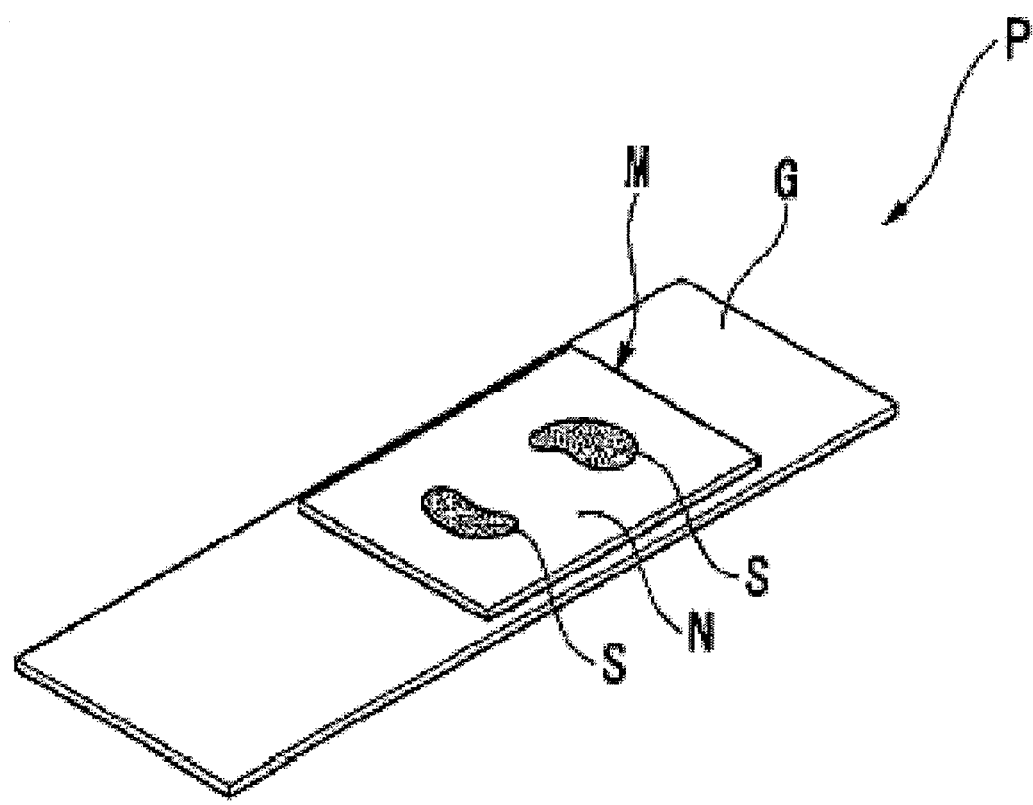
FIG. 2 is a perspective view showing a state in which the thin section shown in FIG. 1 is fixed on a slide glass to yield a thin section slide sample.

Then, the thus manufactured thin section M is subjected to a flattening step for removing the strain generated during thin cutting, such as wrinkles and curls, in which the section is set afloat a liquid such as water and hot water, and scooped thereafter on a substrate G such as a slide glass. Thus, a thin section slide sample P shown in FIG. 2 is obtained by drying off water that had adhered to the section during the flattening.

Figure 3:
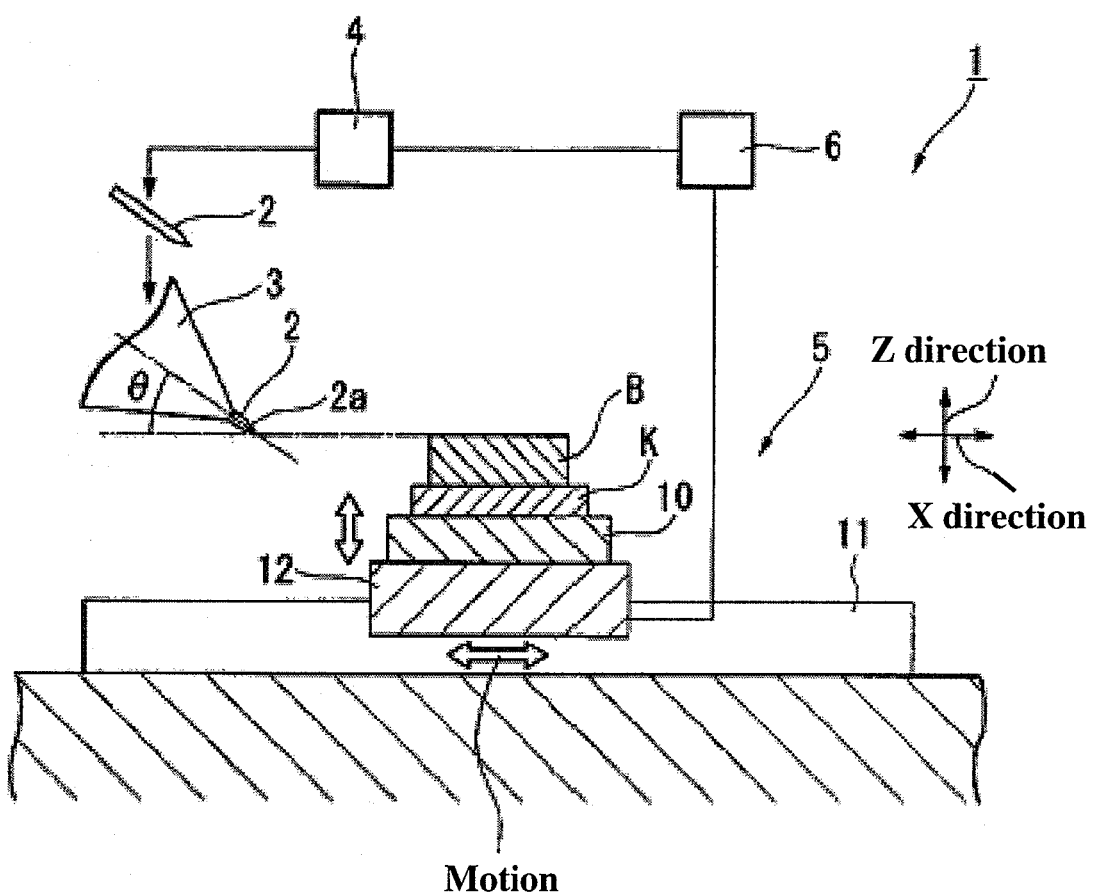
FIG. 3 is a simplified configuration diagram showing an embodiment of an automatic thin-section manufacturing system according to the invention.

The automatic thin-section manufacturing system 1 according to the present embodiment comprises, referring to FIG. 3, a cutting blade 2, a holder 3 for fixing the cutting blade 2 in a freely detachable manner, a conveyor unit 4 for conveying the cutting blade 2 to the holder 3, a transportation unit 5 which moves the embedded block B relative to the holder 3 to thereby perform the cutting out of a thin section M from the embedded block B, and a control unit 6 for total control of these components.

The embedded block B is attached via a cassette K to a Z-axis stage 10 which adjusts the thickness of the thin section M. The Z-axis stage 10 is also installed on a moving stage 12 which moves along a guide rail 11. The guide rail 11 is provided to the water surface, and is extended to a direction X headed to the cutting blade 2. In this case, the guide rail 11 is extended to the opposite side beyond the cutting blade 2. The moving stage 12 is set to reciprocate on the guide rail 11 by a not shown driving source such as a motor. Furthermore, the Z-axis stage 10 comprises embedded therein a not shown piezo element actuator, such that the height is controlled to be elevated for a constant length along the vertical Z direction on applying an electrical voltage. In this case, the Z-axis stage 10 is controlled by the control unit 6 as such that it may be elevated for a constant length while the moving stage 12 reciprocates along the guide rail 11 once.

In this manner, the embedded block B moves towards the cutting blade 2 together with the movement of the moving stage 12, so that it may be cut by the cutting blade 2. In this case, because the height is controlled by the Z-axis stage 10, the surface can be thinly sectioned at a predetermined thickness (for example, 5 μm). As a result, there is obtained a sheet-like thin section M shown in FIG. 1. Thus, plural thin sections M can be obtained sequentially by the reciprocal movement of the moving stage 12 and the elevation of the Z-axis stage 10 which is synchronized to the reciprocal movement.

The guide rail 11, the moving stage 12, and the Z-axis stage 10 described above function as a transportation unit 5 for cutting out the thin section M by moving the embedded block B relative to the holder 3, and by thinly cutting the embedded block B being pressed by a first pressing plate (first pressing member) 22 or a second pressing plate (second pressing member) 23, which are to be described hereinafter.

In the present embodiment, the constitution comprises an embedded block B moved with respect to the cutting blade 2, however, the invention is not only limited thereto. For instance, the transportation unit 5 may be constituted as such that the embedded block B is fixed and the holder 3 is moved, or both the embedded block B and the holder 3 may be moved. At any rate, any constitution is feasible so long as the embedded block B and the holder 3 are moved relative to each other.

Furthermore, in the present embodiment, a case in which Z-axis stage 10 having a piezo element embedded therein is provided as an example; however, the invention is not only limited thereto, and similarly to the moving stage 12, another driving source such as a motor may be used.

Figure 4:
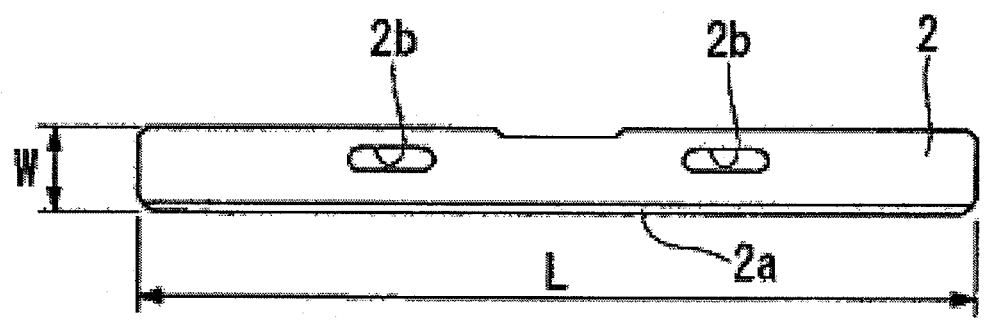
FIG. 4 is a top view of a cutting blade for use in the automatic thin-section manufacturing system shown in FIG. 3.
Figure 5:
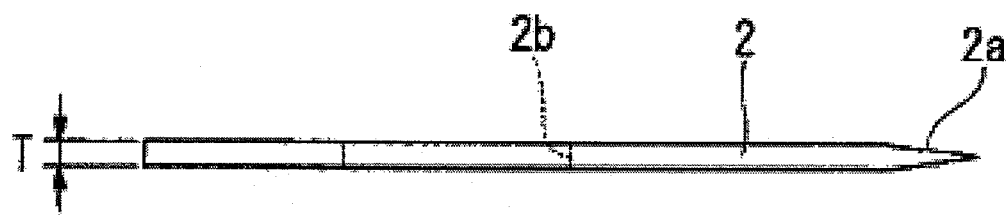
FIG. 5 is a side view of the cutting blade shown in FIG. 4.

As shown in FIGS. 4 and 5, the cutting blade 2 above is such a cutting blade made of a long magnetic body having a cutting edge 2a on one end. The cutting blade 2 comprises two penetrating holes 2b taking an interval. In the present embodiment, a cutting blade 2 having a double-edge as the cutting edge 2a is used as an example. Concerning the size of the cutting blade 2, such having a length L of 80 mm, a width W of 80 mm, and a thickness T of 0.25 mm may be mentioned as an example. Cutting blades 2 having such a constitution are stored and piled to make multiple layers inside a storage case 30, which is described hereinafter. The details are described later.

Figure 6:
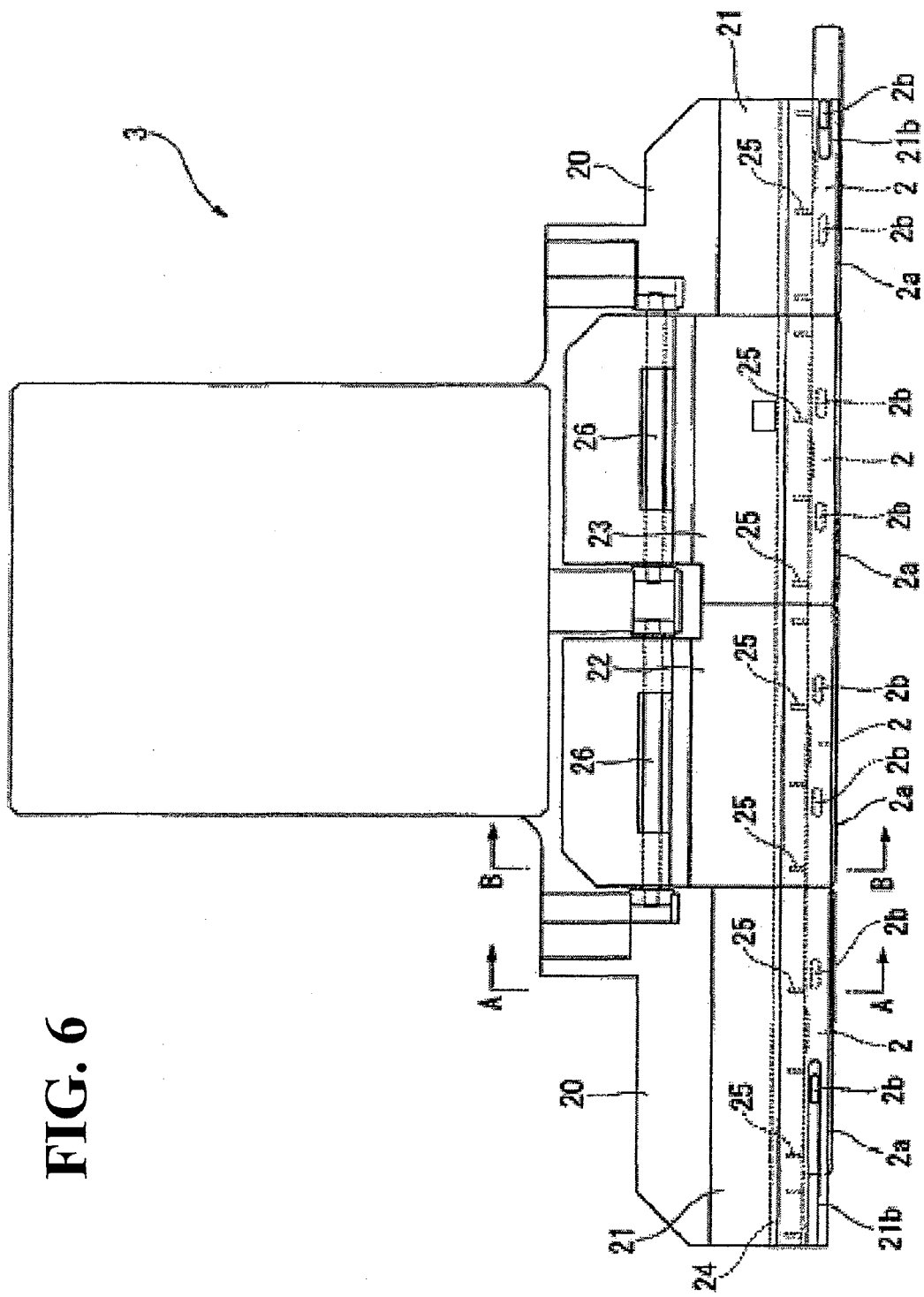
FIG. 6 is a top view of a holder constituting the automatic thin-section manufacturing system shown in FIG. 3.
Figure 7:
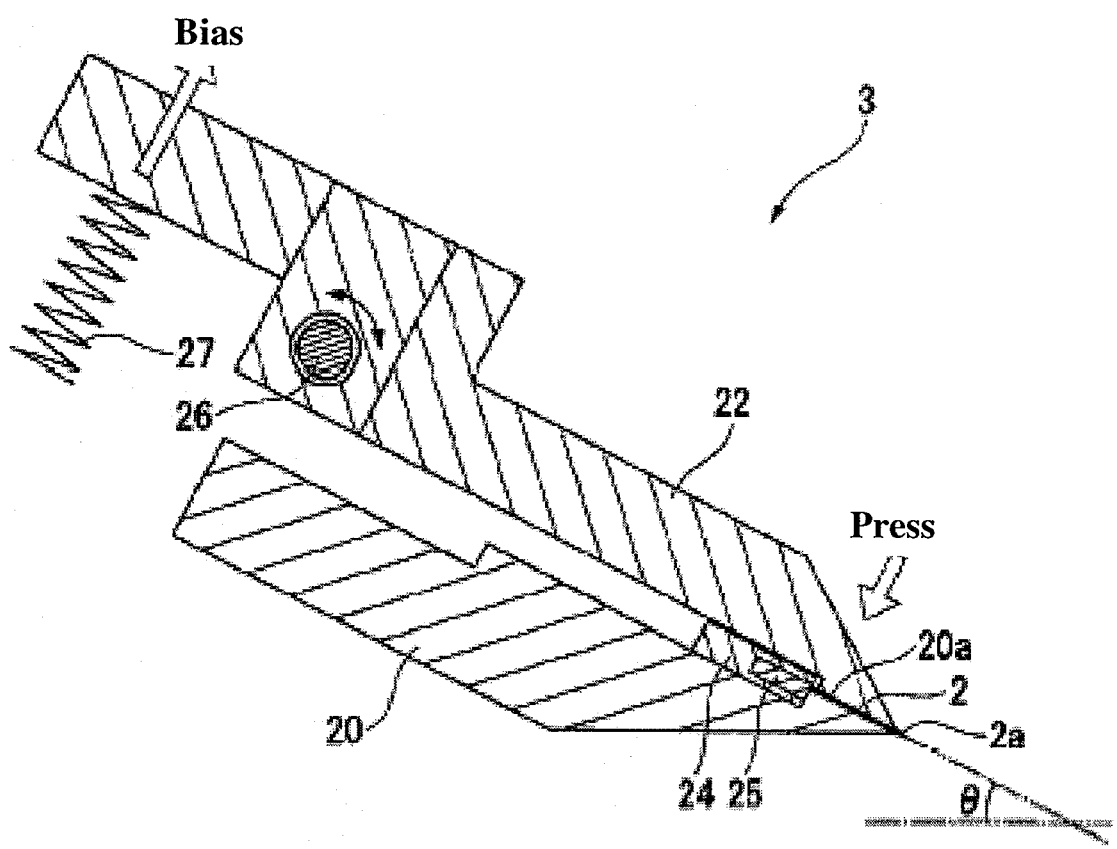
FIG. 7 is a cross section view of the holder shown in FIG. 6, taken along the arrow-indicated line A-A.
Figure 8:
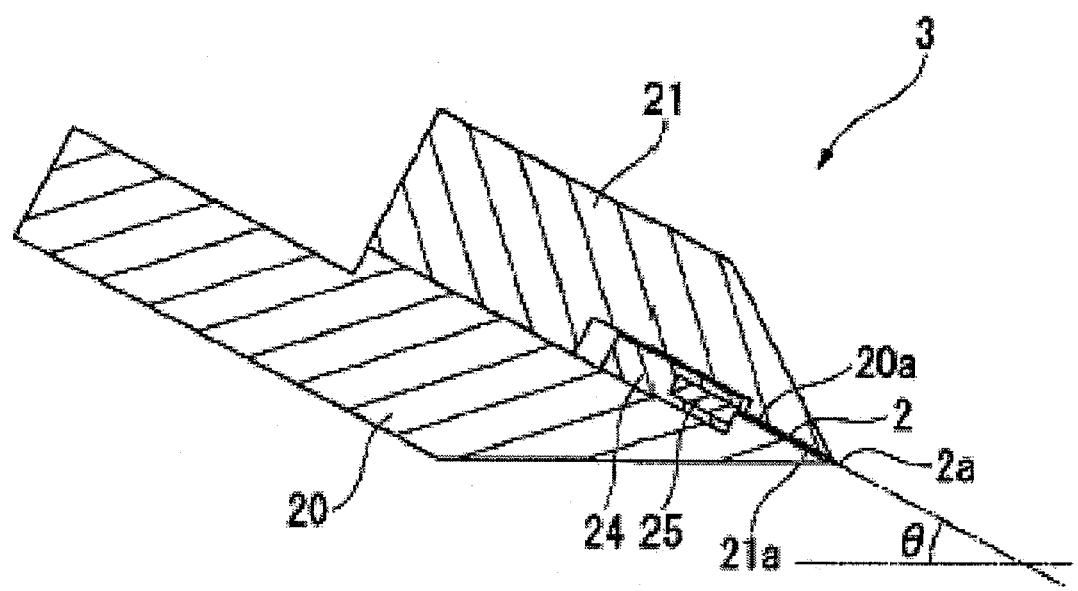
FIG. 8 is a cross section view of the holder shown in FIG. 6, taken along the arrow-indicated line B-B.

Referring to FIGS. 6 to 8, the holder 3 is arranged at a predetermined rake angle θ (for instance, around 27°) with respect to the horizontal plane that is in parallel with the surface of the embedded block B. The lower side plate 20, the upper side plate 21, first pressing plate 22, and a second pressing plate 23 mainly constitute the holder.

The lower side plate 20 is formed in an approximately T-like planar shape having a widened front end. A mounting plane 20a, on which plural cutting blades 2 are mounted in one line with their cutting edges 2a exposed to their outer side, is formed on the front edge of the lower side plate 20. In the present embodiment, four cutting blades 2 are to be mounted at one time.

A sheet plate 24 is joined neighbored to and along the mounting plane 20a of the lower side plate 20. Plural magnets (adsorptive members) 25 are buried and fixed at intervals on the edge plane of the sheet plate 24. The magnets 25 adsorb the base end side (the side opposite to the cutting edge 2a) of the cutting blades 2 mounted on the mounting plane 20a by magnetic force to maintain the posture of the cutting blades 2. By the plural magnets 25, the cutting blades 2 are constantly mounted with their base end sides tightly adhered to the edge plane of the sheet plate 24. In the present embodiment, the number and the interval of the magnets 25 are so adjusted that a single cutting blade 2 may be constantly adhered by 3 or 4 magnets 25 at a time.

The first pressing plate 22 and the second pressing plate 23 are provided neighboring to each other and in approximately the central part of the lower side plate 20. Among the plural cutting blades 2 aligned along the mounting plane 20a, the cutting blade 2 located at a predetermined position is pressed and fixed by both of the pressing plates 22 and 23.

More specifically, referring to FIGS. 6 and 7, the first pressing plate 22 is connected in a freely rotatable manner to a shaft 26 fixed to the lower side plate 20. Further, a coil spring 27 is provided between the lower side plate 20 and one side end of the first pressing plate 22 for biasing. Thus, on receiving the spring force of the coil spring 27, the front edge side of the first pressing plate 22 rotates around the shaft 26 and is pushed towards the mounting plane 20a. As a result, as described above, the cutting blades 2 are pushed against the mounting plane 20a and fixed.

Furthermore, the first pressing plate 22 is set as such that one side end is pushed by a not shown rod which operates in accordance with the command from the control unit 6, with a force which acts against the coil spring 27. Accordingly, the front end side rotates around the shaft 26 in the reverse direction as to properly release the pressing applied to the cutting blade 2. The cutting blade 2 pressed by the first pressing plate 22 is used for thinly cutting the embedded block B as the cutting blade 2 for main sectioning.

The description of the second pressing plate 23 is omitted because it is provided in a constitution similar to that of the first pressing plate 22. The cutting blade 2 pressed by the second pressing plate 23 is used for thinly cutting the embedded block B as the cutting blade 2 for preliminary cutting.

Referring to FIGS. 6 and 8, the upper side plate 21 is a plate that is superposed to the lower side plate 20 on the both sides of the first pressing plate 22 and the second pressing plate 23; a plane 21a to be faced to the mounting plane 20a is provided to the front end at an interval slightly larger than the thickness of the cutting blade 2. The cutting blades 2 are mounted enclosed in this interval. Referring to FIG. 6, groove parts 21b are each formed on the upper side plate 21, from the edge part to the mounting plane 20a, at approximately the same width as that of the penetrating holes 2b provided to the cutting blades 2.

Referring to FIGS. 7 and 8, the first pressing plate 22, the second pressing plate 23, the upper side plate 21, and the lower side plate 20 each have their front edge side cut obliquely, and are shaped in such a shape that it gradually forms a peak towards the cutting edge 2a of the cutting blade 2.

The holder 3 thus constituted is set as such that, on receiving the command from the control unit 6, it may slide along the direction tilted to a predetermined angle (for instance, 70°) with respect to the guide rail 11 extended along the X direction. More specifically, the cutting blade 2 pressed by the first pressing plate 22 and the cutting blade 2 pressed by the second pressing plate 23 are slid out to the position corresponding to the trajectory of the embedded block B that is moved by the moving stage 12. In this manner, the embedded block B can be subjected to preliminary cutting or main sectioning by selecting the cutting blade 2. In this instance, the control unit 6 controls the sliding movement of the holder 3, such that the embedded block B may be subjected to preliminary cutting with a cutting blade 2 for preliminary cutting, followed by main sectioning using the cutting blade 2 dedicated for main sectioning.

The conveyor unit 4 above slides out the plural cutting blades 2 aligned in one line on the mounting plane 20a, by conveying them sequentially onto the mounting plane 20a of the holder 3. Thus, referring to FIG. 9, the conveyor unit 4 comprises a storage case 30; a conveyor path 40 set at a rake angle θ and located between the storage case 30 and the holder 3, having a conveyor plane 41a leveled in such a manner that its surface make a flat plane with the mounting plane 20a of the holder 3 to convey thereon the cutting blades 2; and a conveyor mechanism 50 which sends out the cutting blades 2 one by one from the storage case 30 and temporarily mounts the cutting blade 2 on the conveyor plane 41a, and feeds out the cutting blades 2 along the conveyor plane 41a onto the mounting plane 20a.

Figure 10:
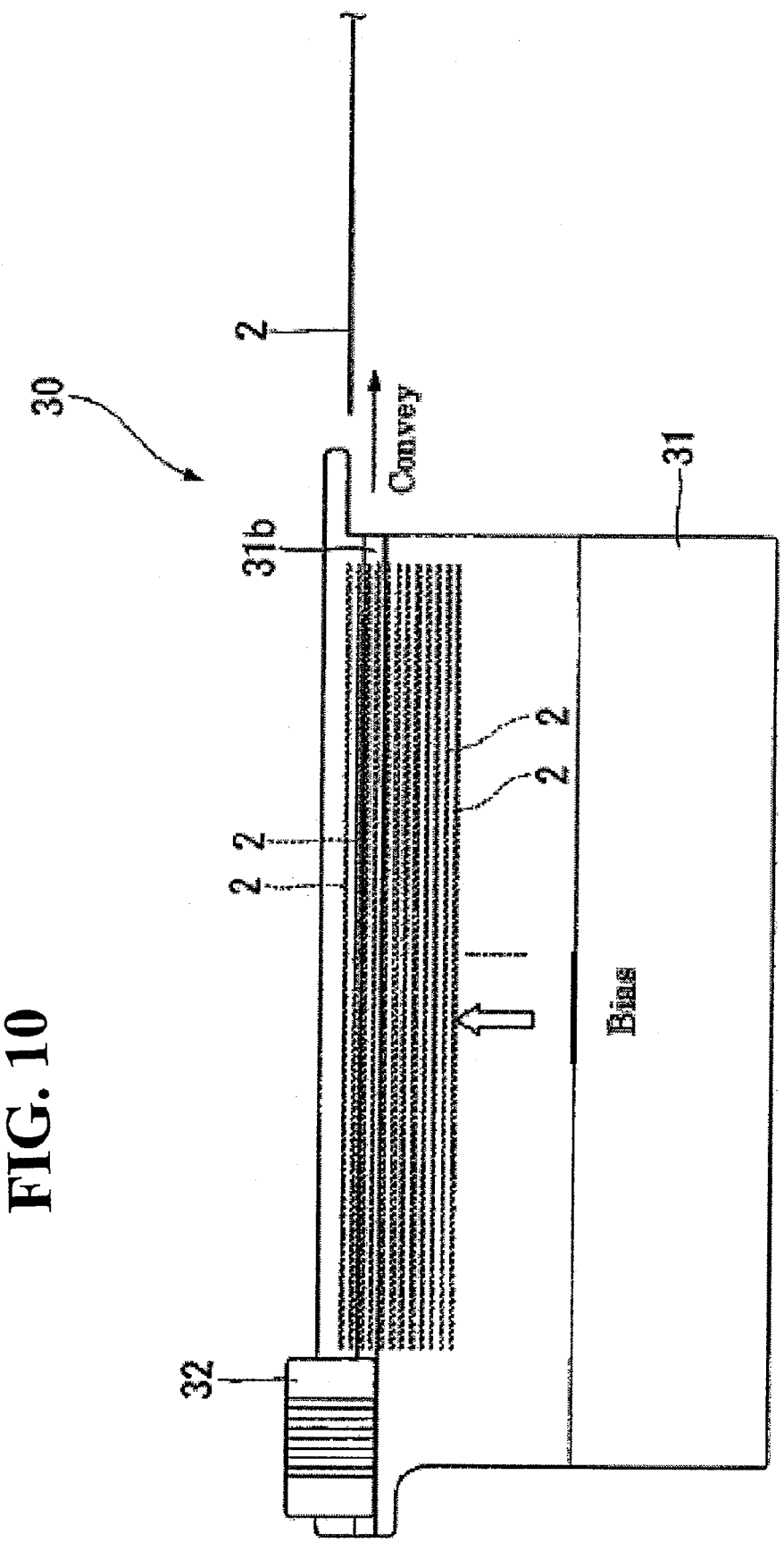
FIG. 10 is a side view of a storage case constituting the conveyor unit shown in FIG. 9.
Figure 11:
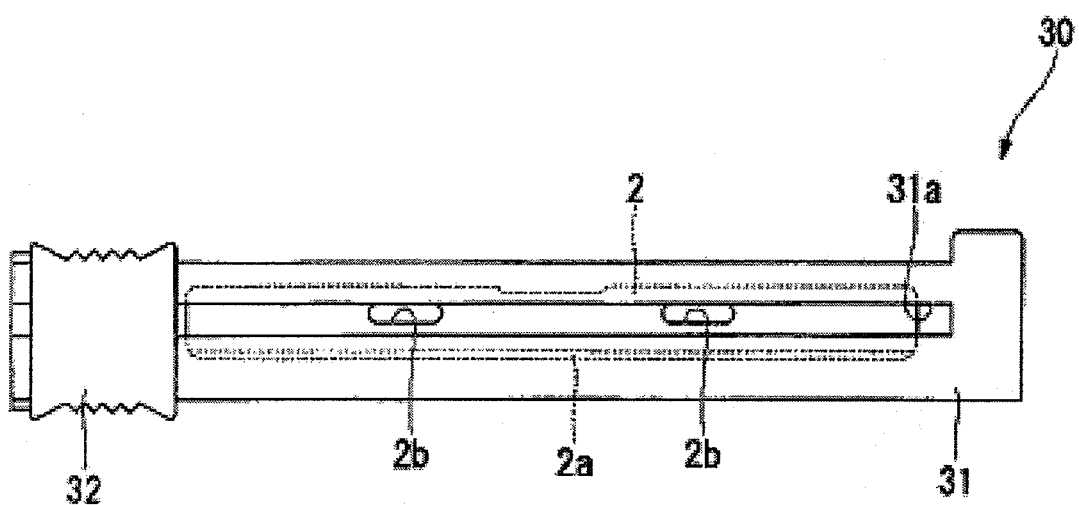
FIG. 11 is a top view of the storage case shown in FIG. 10.
Figure 12:
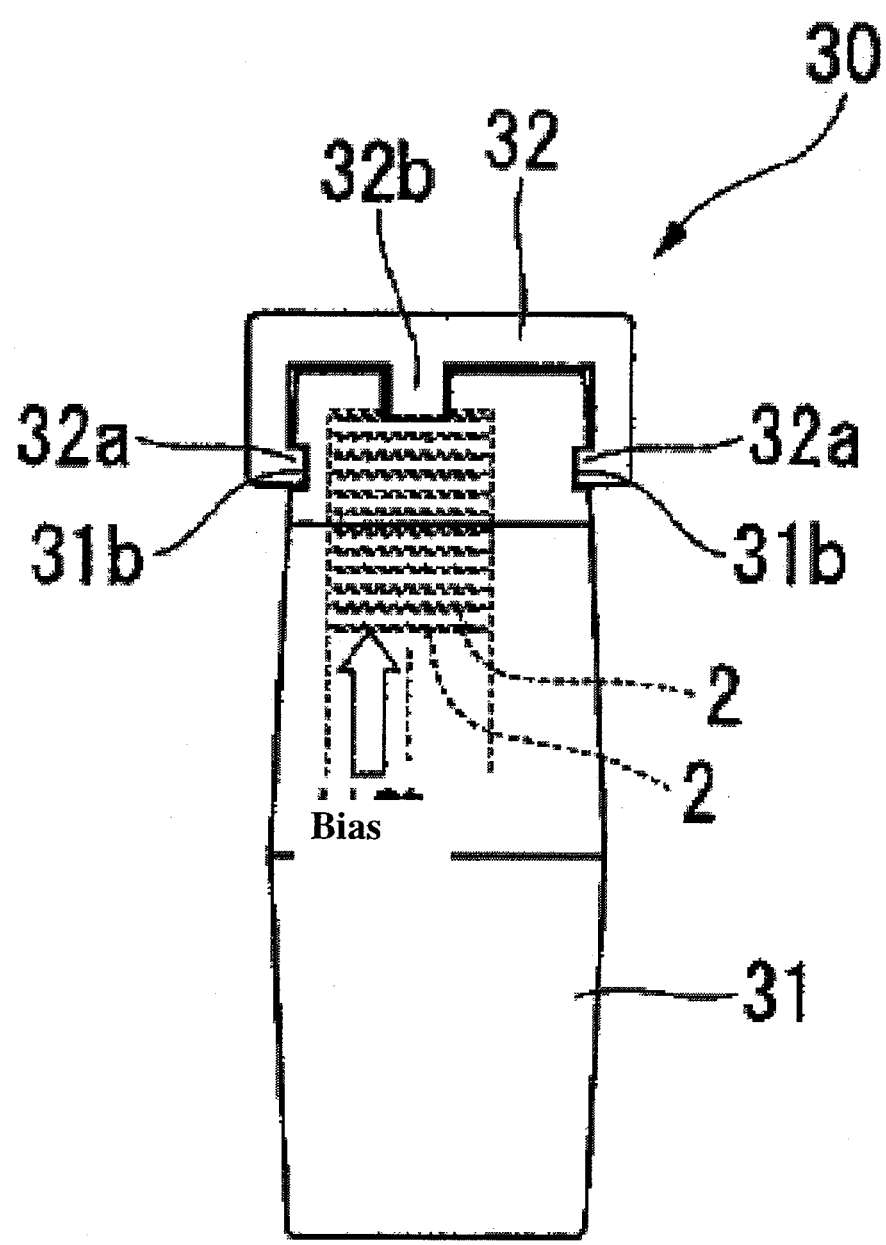
FIG. 12 is a front elevation of the storage case shown in FIG. 10.

Referring to FIGS. 10 to 12, the storage case 30 comprises plural cutting blades 2 stored piled therein to make multiple layers. More specifically, the storage case 30 comprises a casing body 31 and a lever part 32 for taking only one cutting blade 2 out of the casing body 31. The casing body 31 is formed in an approximately rectangular box shape, and a long groove 31a is formed along the longitudinal direction of the surface on the top. Further, the cutting blades 2 stored inside the casing are constantly biased against the top by a not shown biasing unit provided to the bottom part of the casing body 31. Guide grooves 31b are formed along the longitudinal direction of the side planes of the casing body 31 and opposed to each other. Furthermore, a not shown opening, through which the cutting blades 2 are transferred, is formed on the side plane of the casing body 31, such that the cutting blade 2 located at the uppermost position of the pile of cutting blades 2 stored inside the casing body 31 may be sent out to the outside through this opening.

The lever part 32 is formed approximately in a shape having an open angular cross section with three sides, and it covers the top of the casing body 31 with the claw part 32a engaged to a pair of guide grooves 31b. The lever part 32 is set freely movable along the longitudinal direction of the casing body 31 with its claw part 32a guided by the guide grooves 31b. Furthermore, a protrusion 32b is formed on the lever part 32, such that it may intrude inside the long groove 31a formed on the top of the casing body 31. The length of the protrusion 32b is adjusted as such that it may be in contact with only the cutting blade 2 located at the uppermost position of the plural cutting blades 2 stored inside the casing body 31. In this manner, only the cutting blade 2 located at the uppermost position is pushed out by moving the lever part 32, and is sent out to the outside of the casing body 31 through the opening formed on the casing body 31.

The casing body 31 thus constituted is fixed by a not shown table in such a manner that it is tilted at the rake angle θ, such that the upper plane make an angle with respect to the horizontal plane parallel to the surface of the embedded block B corresponding to the rake angle θ.

Figure 13:
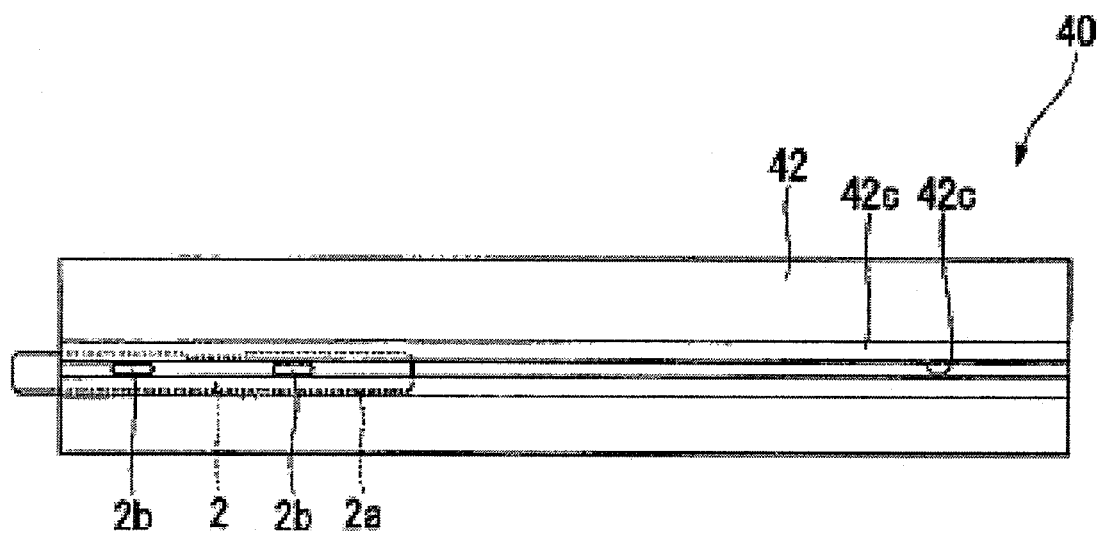
FIG. 13 is a top view of a conveyor path constituting the conveyor unit shown in FIG. 9.
Figure 14:
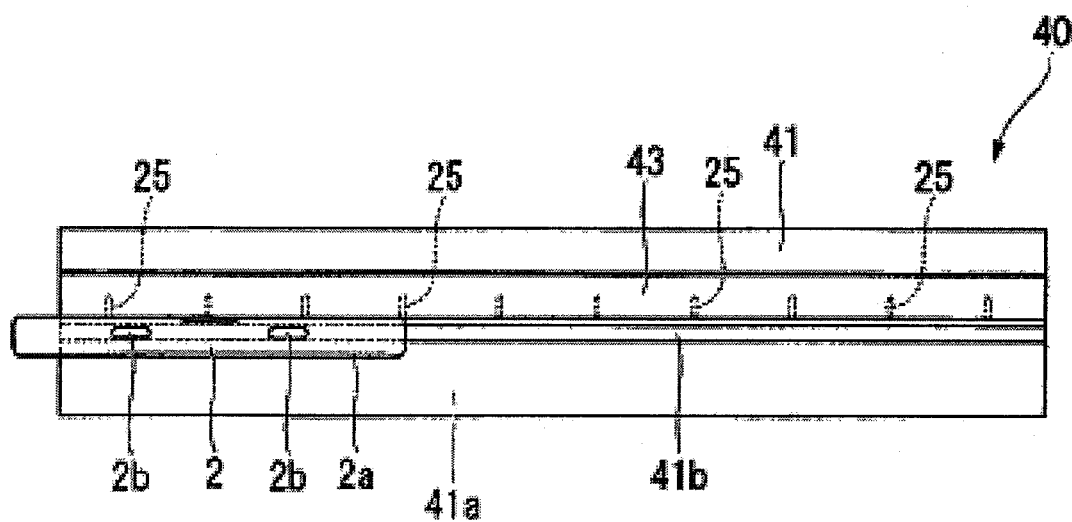
FIG. 14 shows the same view as in FIG. 13, except that the top plate is removed.
Figure 15:
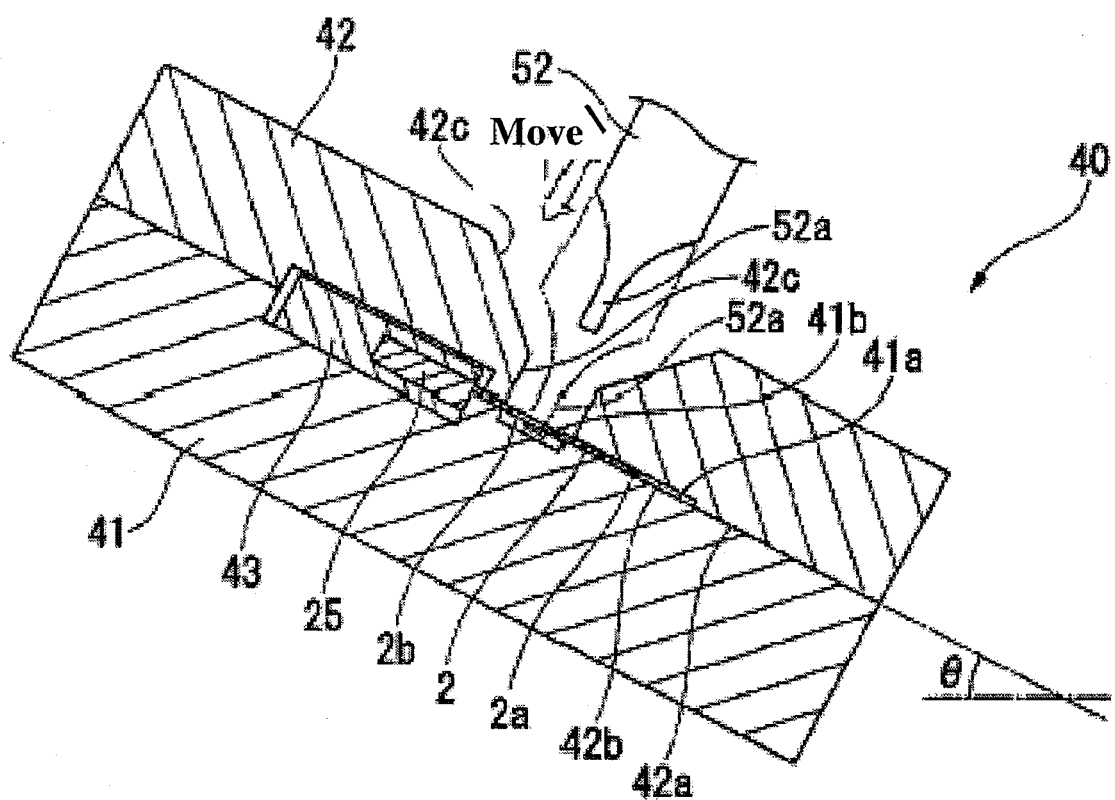
FIG. 15 is a cross section view of the conveyor path shown in FIG. 13.

Referring to FIGS. 13 to 15, the conveyor path 40 comprises a lower side plate 41 and an upper side plate 42 engaged in such a manner that it may be superposed to the lower side plate 41. Further, a part of the upper plane of the lower side plate 41 is set as the conveyor plane 41a. Moreover, a sheet plate 43 is joined to the lower side plate 41, neighbored to and along the conveyor plane 41a. Plural magnets 25 are buried and fixed at intervals on the edge plane of the sheet plate 43. The magnets 25 adsorb the base end side (the side opposite to the cutting edge 2a) of the cutting blades 2 mounted on the mounting plane 41a by magnetic force to maintain the posture of the cutting blades 2. By the plural magnets 25, the cutting blades 2 are constantly mounted with their base end sides tightly adhered to the edge plane of the sheet plate 43. Furthermore, a groove part 41b (which is described hereinafter), which engages with the front end part 52a of the second conveyor lever 52, is formed along the longitudinal direction on the conveyor plane 41a. The groove part 41b is formed at a width somewhat larger than the width of the penetrating holes 2b provided to the cutting blade 2.

The upper side plate 42 is superposed to cover the entire lower side plate 41. A concave part 42b, which makes a space for enclosing the cutting blade 2 when superposed, is formed along the longitudinal direction on the facing plane 42a disposed opposed to the lower side plate 41. Thus, when enclosed in the space, the cutting blade 2 is mounted on the conveyor plane 41a and conveyed. Furthermore, similar to the case of lower side plate 41, a penetrating groove 42c for engaging the front end part 52a of the second conveyor lever 52, as described hereinafter, is also formed along the longitudinal direction of the upper side plate 42.

The conveyor path 40 made up as stated above is fixed on the base plate 53 provided to the mechanism 50, which is described hereinafter, in a tilted state at a rake angle θ as stated above, i.e., such that the conveyor plane 41a make an angle with respect to the horizontal plane parallel to the surface of the embedded block B corresponding to the rake angle θ. In this case, the position of the conveyor path 40 is adjusted as such that the conveyor plane 41a is set to the same level as that of the bottom plane of the cutting blade 2 located at the uppermost position in the storage case 30, and is set at the same time to be at the same level of the mounting plane 20a of the holder 3.

Referring to FIGS. 16 to 19, the conveyor mechanism 50 above is equipped with a first conveyor lever 51 and a second conveyor lever 52; by using both of the conveyor levers 51 and 52, a cutting blade 2 is conveyed out from the storage case 30, and the cutting blade 2 is delivered along the conveyor plane 41a to be fed onto the mounting plane 20a of the holder 3. In this case, the conveyor mechanism 50 sends out the cutting blade 2 to the conveyor plane 41a from the storage case 30 using the first conveyor lever 51, and at the same time, the cutting blade 2 taken out by the second conveyor lever 52 is conveyed along the conveyor plane 41a to be fed onto the mounting plane 20a. Thus, the conveyor mechanism 50 appropriately uses the two conveyor levers 51 and 52 to convey the cutting blades 2.

In further detail, a guide rail 54 is fixed on the base plate 53 having thereon the fixed conveyor path 40, in such a manner that it may be in parallel with the conveyor path 40. A linear guideway 55, which is movable along the guide rail 54, is fixed to the guide rail 54. A moving plate 56 is also fixed to the linear guideway 55.

A pair of pulleys 57 and 58 is fixed to the base plate 53, and a conveyor belt 59 is wound around the pair of pulleys 57 and 58. In this case, the positions of the pair of pulleys 57 and 58 are adjusted as such that the conveyor belt 59 may move along in the direction parallel to the guide rail 54. Furthermore, one of the pair of pulleys 57 and 58, the pulley 57, is connected to a driving motor 60 so that it may be rotated together with the operation of the driving motor 60. Thus, the conveyor belt 59 is set to make a reciprocal movement along a direction in parallel with the guide rail 54.

The moving plate 56 is connected to the conveyor belt 59, such that it may reciprocate in conjunction with the movement of the conveyor belt 59. Since the moving plate 56 is guided by the guide rail 54 via the linear guideway 55 in this case, it can be moved smoothly free of vibration and the like. The details are described below by taking the position at which the moving plate 56 is at the nearest to one pulley 57 (the state shown in FIG. 16) as the initial position.

Two driving motors 61 and 62 are fixed to one end plane of the moving plate 56. The output shafts 61a and 62a of the two driving motors 61 and 62 penetrate the moving plate 56, and are connected to cam plates 63 and 64 located at the other end plane of the moving plate 56. The cam plates 63 and 64 have their outer shapes tailored as such that their distances from the axial lines L of the output shafts 61a and 62a change. That is, the cam plates 63 and 64 rotate eccentrically around the axial lines L of the output shafts 61a and 62a. Furthermore, a first L-shaped angle 65 and a second L-shaped angle 66 are each mounted on the two cam plates 63 and 64, respectively, via rotary rollers 67 and 68. The rotary rollers 67 and 68 are each fixed rotatable to each of the L-shaped angles 65 and 66.

Thus, on eccentrically rotating the cam plates 63 and 64 by operating the driving motors 61 and 62, both L-shaped angles 65 and 66 move linearly via the rotary rollers 67 and 68. That is, the cam plates 63 and 64, and the rotary rollers 67 and 68 each function as a conversion mechanism for converting the rotary force of the driving motors 61 and 62 into a linear motion.

Furthermore, a linear guide 71, which moves along the guide rail 70 fixed to the other end side of the moving plate 56, is attached to both of the L-shaped angles 65 and 66. Accordingly, both L-shaped angles 65 and 66 each make a smooth linear motion guided by the guide rail 70 according to the rotation of the cam plates 63 and 64.

In addition, the two L-shaped angles 65 and 66 each make a separate linear motion depending on the operation of the two driving motors 61 and 62, except for the movement in the direction parallel to the guide rail 54, in which the two L-shaped angles 65 and 66 move simultaneously with the movement of the moving plate 56.

Concerning the two L-shaped angles 65 and 66, the first L-shaped angle 65 comprises fixed thereto the first conveyor lever 51 described above. The conveyor lever 51 is formed in the shape of a plate; so, when the moving plate 56 is located at the initial position and the first L-shaped angle 65 is located at the lowermost position (i.e., the position nearest to the conveyor path 40), it can be lowered to the position capable of being engaged with the lever part 32 of the storage case 30. Thus, by moving the moving plate 56 together with the conveyor belt 59 in this state, it can be moved while pressing the lever part 32 via the first L-shaped angle 65 and the conveyor lever 51, thus feeding one cutting blade 2 from the casing body 31. Thus a cutting blade 2 is fed and mounted on the conveyor plane 41a of the conveyor path 40.

On the other hand, concerning the two L-shaped angles 65 and 66, the second L-shaped angle 66 comprises fixed thereto the linear plate 72 described above, to which the second conveyor lever 52 is fixed to the front edge thereof. The length of the linear plate 72 is adjusted as such that, when the moving plate 56 is located at the initial position, the second conveyor lever 52 is located at the upper side of the penetrating hole 2b of the cutting blade 2 that is mounted on the conveyor plane 41a. Further, the base end side of the second conveyor lever 52 is formed into a cylindrical shape and the front end part 52a thereof is drawn so that it may pass through the penetrating hole 2b of the cutting blade 2.

Figure 16:
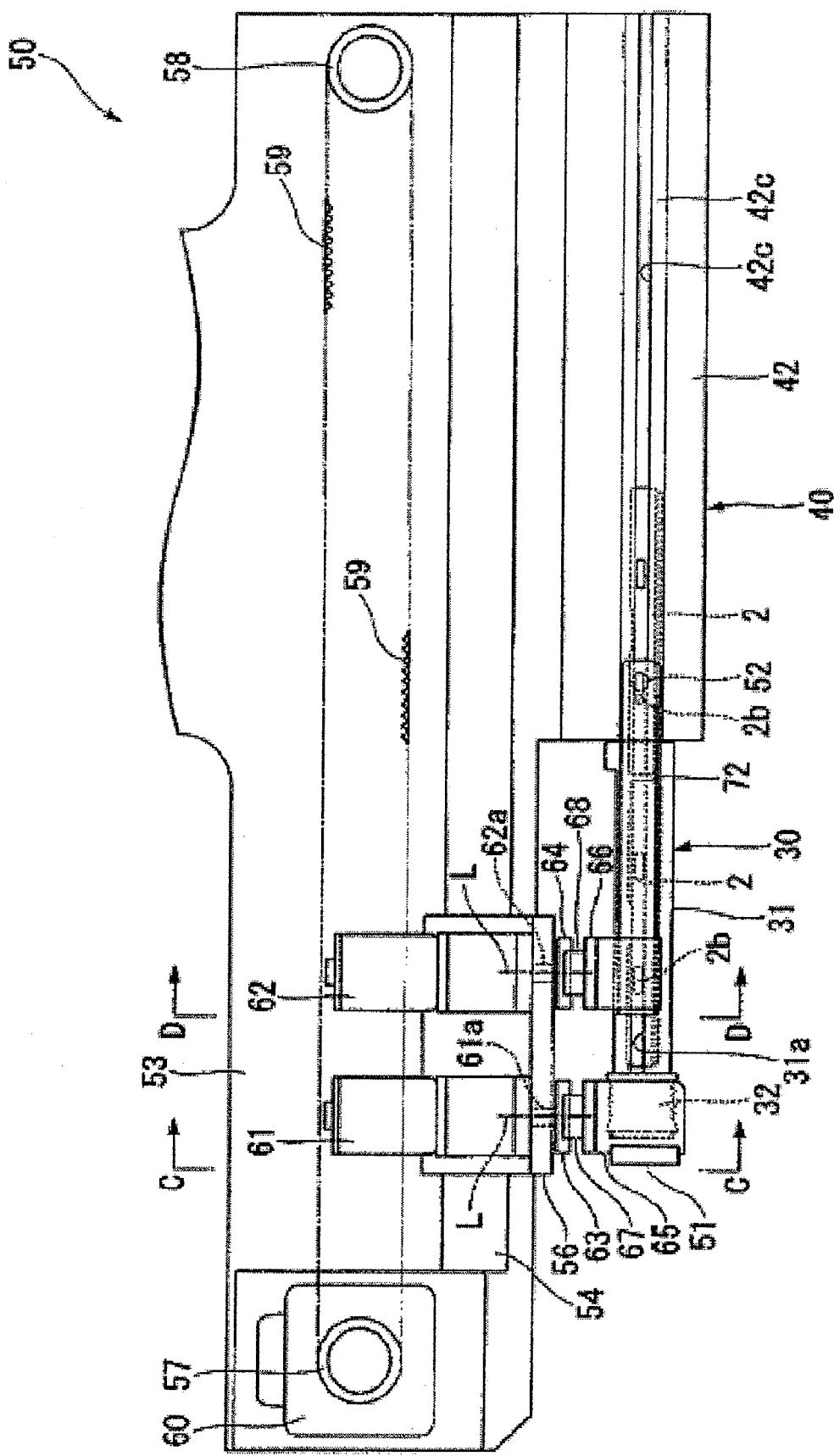
FIG. 16 is a top view of the conveyor mechanism constituting the conveyor unit shown in FIG. 9.

In case the second L-shaped angle 66 is located at the lowermost point, as shown in FIG. 15, the second conveyor lever 52 penetrates the penetrating hole 2b of the cutting blade 2 while the front end part 52a engages with the penetrating groove 42c of the upper side plate 42. At this moment, the front end part 52a of the second conveyor lever 52 intrudes into the groove part 41b of the lower side plate 41. Thus, the front end part 52a of the second conveyor lever 52 is engaged to the penetrating hole 2b of the cutting blade 2 without making contact to the conveyor path 40. Accordingly, as shown in FIG. 16, by moving the moving plate 56 together with the conveyor belt 59 in this state, the cutting blade 2 can be moved via the second L-shaped angle 66, linear plate 72, and the second conveyor lever 52, to be conveyed along the conveyor plane 41a.

Figure 9:
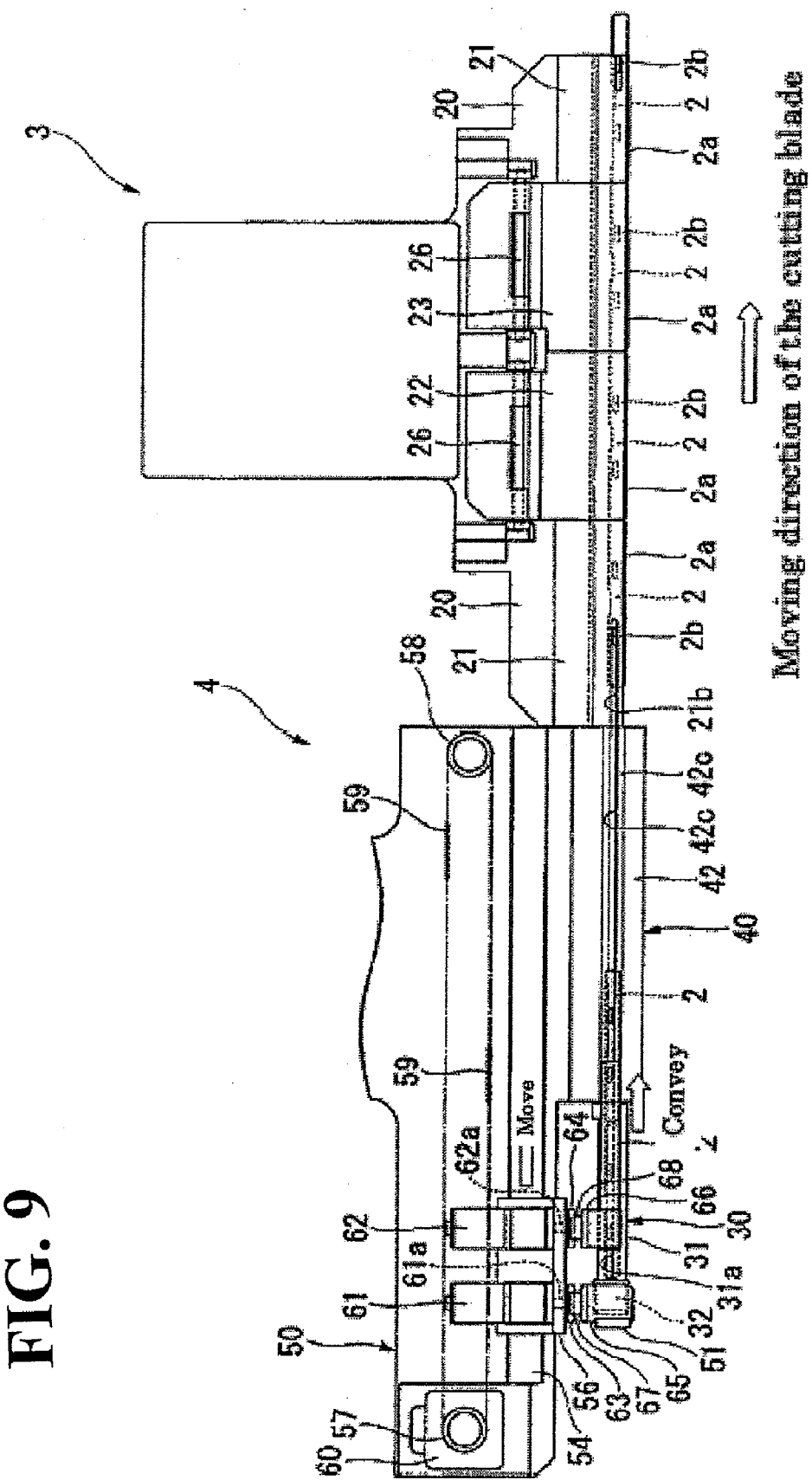
FIG. 9 is a top view of a holder and a conveyor unit constituting the automatic thin-section manufacturing system shown in FIG. 3.

As shown in FIG. 9, by this convey, the cutting blade 2 is fed from the conveyor path 40 onto the mounting plane 20a of the holder 3. In this case, the front end part 52a of the second conveyor lever 52 is brought into a state that is engaged into the groove part 21b formed on the upper side plate 21 of the holder 3. Accordingly, the cutting blade 2 is surely conveyed to the mounting plane 20a of the holder 3.

As described above, the conveyor unit 4 appropriately uses the first conveyor lever 51 and the second conveyor lever 52 of the conveyor mechanism 50; it sends out the cutting blades 2 one by one from the storage case 30, delivers along the conveyor plane 41a, and feeds them to the mounting plane 20a of the holder 3. By repeating these operations, the cutting blades 2 can be sequentially fed one by one onto the mounting plane 20a, and the cutting blades 2 are slid to align in one line on the mounting plane 20a.

Furthermore, the operation of the conveyor unit 4 described above is controlled by a control unit 6. More specifically, the driving motor 60 for driving the pulley 57, and the driving motors 61 and 62 for linearly moving the two L-shaped angles 65 and 66, are all controlled by the control unit 6.

In such a case, when the sectioning operation by the transportation unit 5 is completed by repeating the operation for predetermined times, the control unit 6 is programmed as such that each of the driving motors 60, 61, and 62 in the conveyor unit 4 is operated to convey a new cutting blade 2, so that the cutting blade 2 used for sectioning is exchanged by slide movement. The details thereof are described hereinafter.

A case of manufacturing a thin section M from an embedded block B by utilizing the thus constructed automatic thin-section manufacturing system 1 is described below.

First, at the initial state, the embedded block B is fixed on a moving stage 12 via a cassette K, and the height thereof is adjusted optimally by the Z-axis stage 10. Further, plural cutting blades 2 are piled to make multiple layers in the storage case 30. The two L-shaped angles 65 and 66 of the conveyor mechanism 50 are both located at the uppermost point (the position farthest from the conveyor path 40). The moving plate 56 is located at the initial state.

The thin cutting of the embedded block B starts under the initial state described above.

Figure 18:
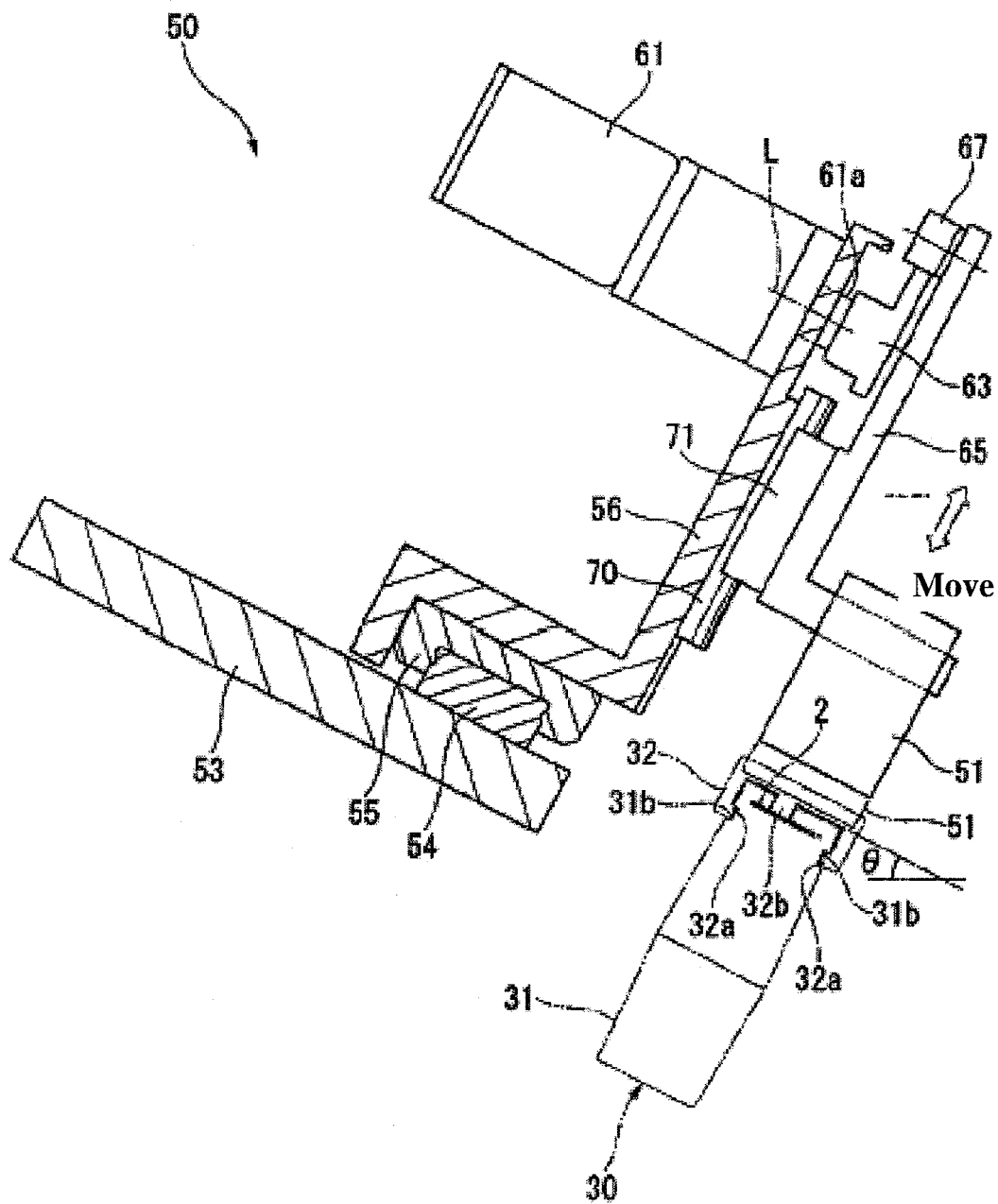
FIG. 18 is a cross section view of the conveyor mechanism, taken along the arrow-indicated line C-C.

First, the control unit 6 operates the driving motor 61 to effect half revolution of the cam plate 63. Thus, as shown in FIG. 18, via the rotary roller 67, the first L-shaped angle 65 travels linearly from the uppermost position to the lowermost position. Then, the first conveyor lever 51 fixed to the first L-shaped angle 65 descends to the position at which it may be engaged with the lever part 32 of the storage case 30. Since the first L-shaped angle 65 moves smoothly along the guide rail 70, similarly, the first conveyor lever 51 moves smoothly free of vibration and the like.

Figure 17:
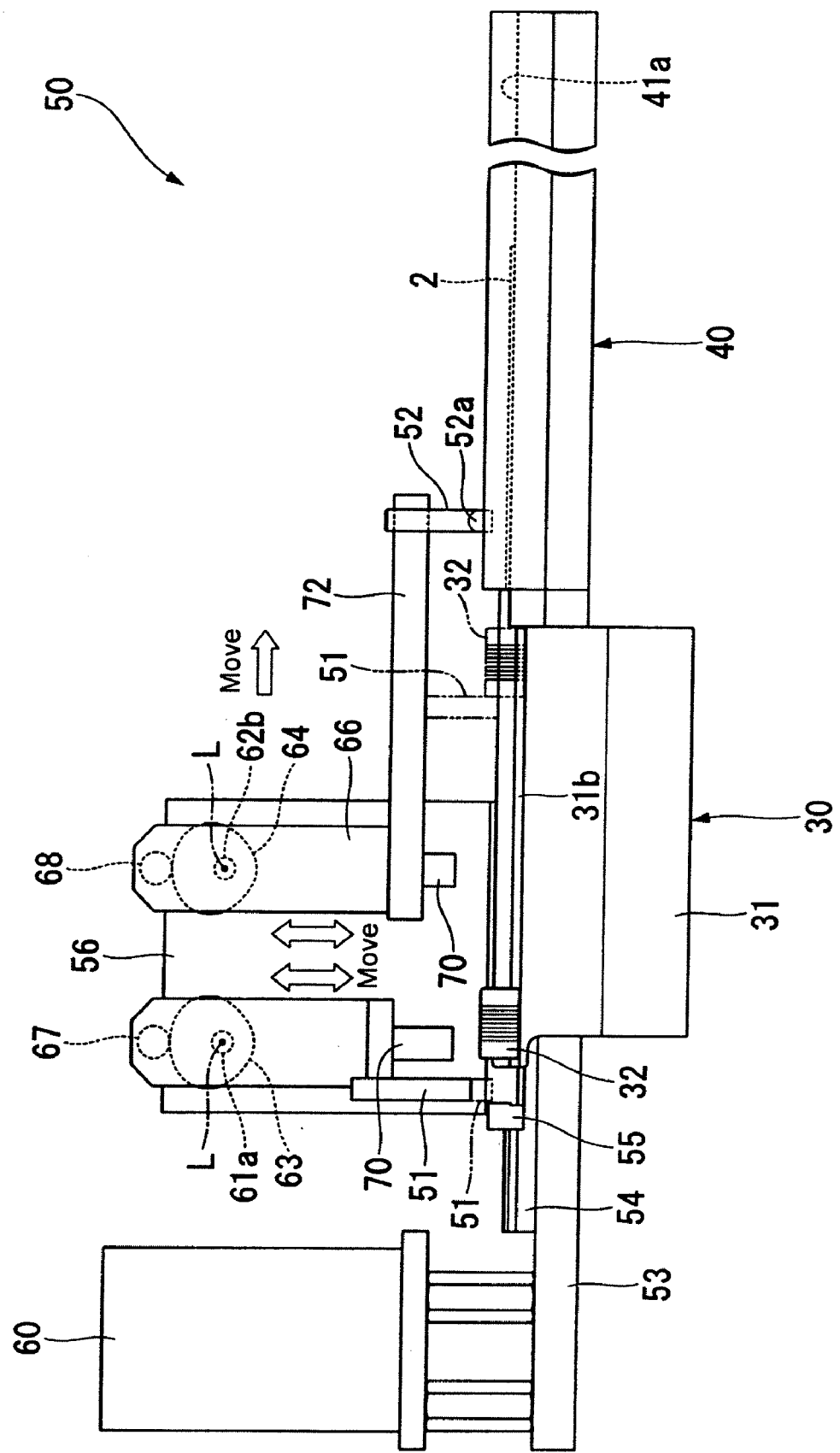
FIG. 17 is a side view of the conveyor mechanism shown in FIG. 16.

Then, the control unit 6 operates the driving motor 60 to rotate the pulley 57. Then, the moving plate 56 moves together with the conveyor belt 59 towards the holder 3. In this manner, as shown in FIG. 17, the first conveyor lever 51 fixed to the first L-shaped angle 65 can be moved to further move the lever part 32 of the storage case 30 towards the conveyor path 40. Thus, among the plural cutting blades 2 stored inside the casing body 31, the cutting blade 2 located at the uppermost position is pushed out by the protrusion 32b formed on the lever part 32 to be sent out of the casing body 31 via the opening.

In this manner, the conveyor mechanism 50 conveys one cutting blade 2 out from the storage case 30, and at the same time, temporarily mounts the thus sent out cutting blade 2 on the conveyor plane 41a of the conveyor path 40.

After conveying out one cutting blade 2, the control unit 6 operates the driving motor 61 again to further half-rotate the cam plate 63. Thus, via the rotary roller 67, the first L-shaped angle 65 moves linearly upward from the lowermost point to the uppermost point. In this way, the first conveyor lever 51 returns back to the original position, at which the joint with the first conveyor lever 51 is released.

Subsequently, the control unit 6 operates the driving motor 60 to move the conveyor belt 59 and the moving plate 56 in the reverse direction, so as to locate, as shown in FIG. 16, the second conveyor lever 52 at the upper side of the penetrating hole 2b formed on the cutting blade 2 mounted on the conveyor plane 41a.

Figure 19:
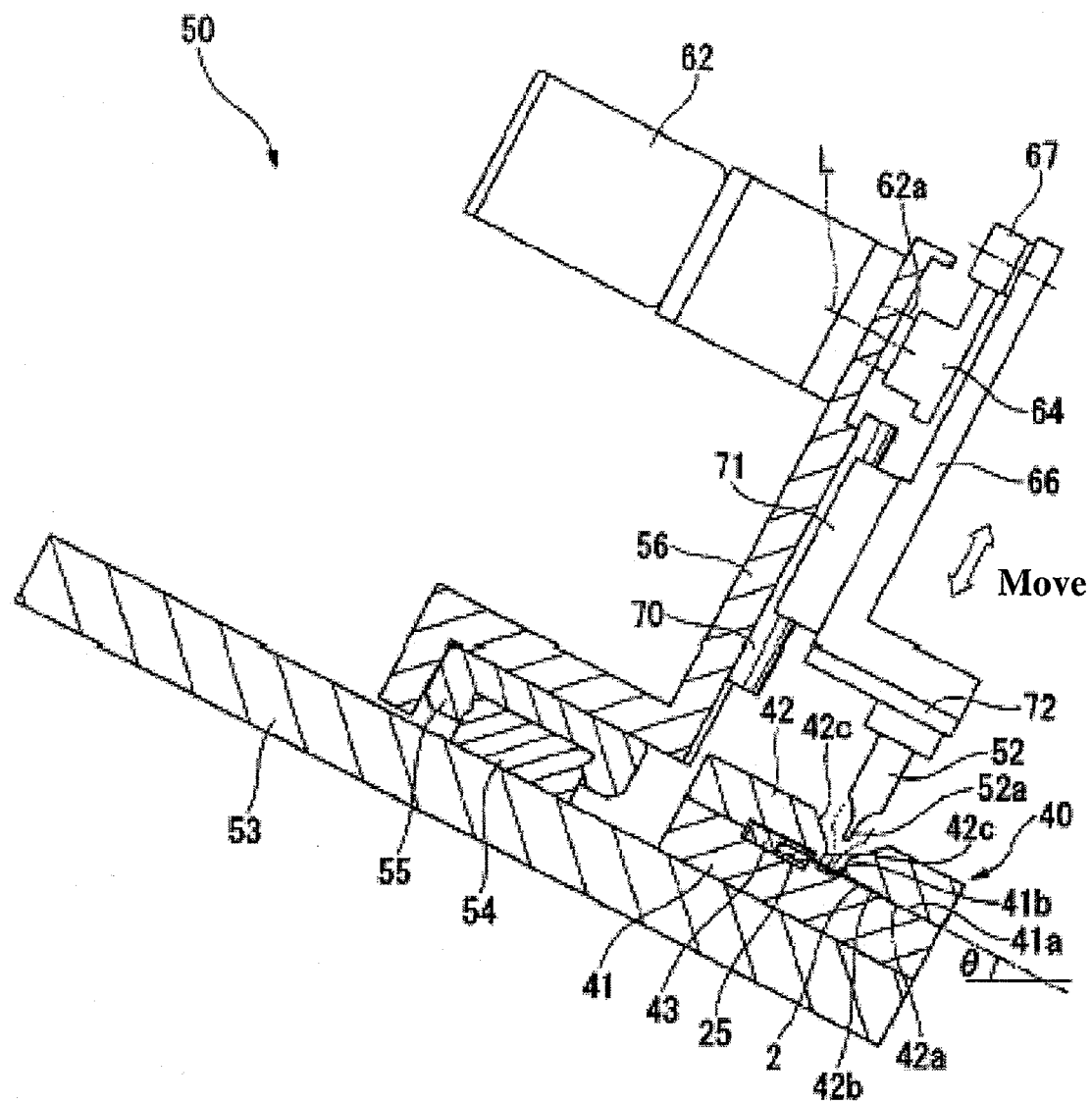
FIG. 19 is a cross section view of the conveyor mechanism, taken along the arrow-indicated line D-D.

Then, the control unit 6 operates the driving motor 62 to half-rotate the cam plate 64. In this manner, as shown in FIG. 19, the second L-shaped angle 66 moves linearly downward from the uppermost point to the lowermost point via the rotary roller 68 in a way similar to that of the previously operated first L-shaped angle 65. Accordingly, the front end part 52a of the second conveyor lever 52 fixed to the second L-shaped angle 66 via the linear plate 72 penetrates through the penetrating hole 2b formed on the cutting blade 2, while entering into the penetrating groove 42c provided to the upper side plate 42. At this moment, the front end part 52a provided to the second conveyor lever 52 is in such a state that a part thereof is engaged to the inside of the groove part 41b of the lower side plate 41.

Subsequently, the control unit 6 rotates the pulley 57 by a driving motor 60 in a manner similar to that described hereinbefore, to thereby move the moving plate 56 together with the conveyor belt 59 towards the holder 3. Thus, the second conveyor lever 52 fixed to the second L-shaped angle 66 can be moved. At this moment, the second conveyor lever 52 moves while pushing the edge plane of the penetrating hole 2b formed on the cutting blade 2, so that the cutting blade 2 may be delivered along the conveyor plane 41a as it is to be fed onto the mounting plane 20a provided on the holder 3. In particular, the conveyor path 40 is set at a rake angle θ similar to the holder 3, and the conveyor plane 41a is set at the same level as that of the mounting plane 20a. Thus, the cutting blade 2 already set at the rake angle θ can be fed out to the mounting plane 20a as it is.

Furthermore, because plural magnets 25 are provided to the conveyor path 40 along the conveyor plane 41a, the base end side of the cutting blade 2 remains adsorbed from the instance the cutting blade 2 is mount on the conveyor plane 41a up to the point at which it is fed out to the holder 3. Thus, the cutting blade 2 stably maintains the posture during convey, free from being dropped off by the gravimetric force.

Accordingly, the cutting blade 2 set at the rake angle θ can be surely fed onto the mounting plane 20a. Furthermore, because the base end side is adsorbed by the magnets 25, the cutting edge 2a is never brought into contact with the upper side plate 42 during convey. Thus, the cutting blade 2 can be fed to the holder 3 side while maintaining its quality.

The cutting blade 2 fed onto the mounting plane 20a of the holder 3 is mounted in such a state as shown in FIGS. 6 and 8, in which the cutting edge 2a is exposed. Moreover, similar to the case of the conveyor path 40, the cutting blade 2 is in such a state that the base end side is adsorbed by plural magnets 25 provided along the mounting plane 20a. Accordingly, even if the holder 3 is tilted at the rake angle θ, the cutting blade 2 remains its stable posture without sliding off the mounting plane 20a, free from being influenced by the gravitational force.

As described above, the control unit 6 delivers the first cutting blade 2 to the mounting plane 20a of the holder 3, and then, controls the conveyor unit 4 to repeat a similar motion to deliver the second cutting blade 2 to the mounting plane 20a. Then, because the second delivered cutting blade 2 pushes the first delivered cutting blade 2, the first one is moved along the mounting plane 20a. More specifically, the cutting blades 2 slide along the mounting plane 20a in an aligned state.

Furthermore, the cutting blade 2 not only is simply mounted on the mounting plane 20a, but is mounted enclosed inside a space formed by the upper side plate 21 and the lower side plate 20. Accordingly, no overriding occurs in case the second cutting blade 2 pushes the first cutting blade 2. Thus, slide movement is assured by pushing the first cutting blade 2.

Then, when the slid out cutting blade 2 is located at the predetermined position of the mounting plane 20a, as shown in FIG. 7, it is tightly pressed by the first pressing plate 22 against the mounting plane 20a and fixed. In this manner, the thus pressed cutting blade 2 can be used as the cutting blade 2 for main sectioning. Furthermore, because the cutting blade 2 slid out with its posture stabilized by the magnets 25, the amount of protrusion of the cutting edge 2a exposed from the holder 3 can be kept at a predetermined value.

Then, by fixing the cutting blade 2, the control unit 6 moves the moving stage 12 along the guide rail 11 as shown in FIG. 3. At this moment, the embedded block B can be cut by using the thus press-fixed cutting blade 2 dedicated for sectioning. Thus is obtained a thin section M from the embedded block B. Furthermore, because a cutting blade 2 set at a predetermined rake angle θ can be used, sectioning can be smoothly performed. In addition, high quality thin sections M can be obtained, because, as described above, the amount of protrusion of the cutting edge 2a is maintained constant.

Further, after sectioning is completed for predetermined times, the control unit 6 operates a not shown rod to press one end of the first pressing plate 22 with a force resistant to the spring coil 27. In this manner, the cutting blade 2 can be released from the press. At the same time, the control unit 6 operates the conveyor unit 4 to convey a new cutting blade 2 onto the mounting plane 20a. In this manner, the used cutting blade 2 remaining mounted on the mounting plane 20a is pushed by the new cutting blade 2 and slides out of the mounting plane 20a. Then, when a new cutting blade 2 is located to the predetermined position, the first pressing plate 22 presses the cutting blade 2 to provide a cutting blade 2 dedicated for sectioning.

That is, the cutting blades 2 are automatically exchanged every predetermined times of sectioning. Accordingly, the cutting blades are exchanged without involving any manpower; hence, the burden on the operators can be minimized.

Furthermore, high quality thin sections M can be manufactured because sharp-edged cutting blades 2 are provided constantly.

Concerning the exchanged cutting blade 2, similar to the case above, the amount of protrusion of the cutting edge 2a is also set at a predetermined value. Accordingly, the cutting blade 2 can be exchanged while reducing the fluctuations in the cutting edges 2a. Thus, thin sectioning of the embedded block B can be constantly carried out under the same conditions even if the cutting blade 2 is exchanged, and hence, thin sections M of the same quality can be continuously manufactured.

When the cutting blade 2 dedicated for main sectioning and which was previously used for sectioning is moved by the conveyor unit 4, the second pressing plate 23 re-presses and tightly fixes the cutting blade 2 against the mounting plane 20a. In this manner, the cutting blade 2 once used for sectioning can be reused as a cutting blade 2 for preliminary cutting.

For instance, in case the embedded block B is exchanged into a new one, preliminary cutting is carried out at first before performing main sectioning. In such a case, the control unit 6 moves the holder 3 and adjusts its position so that the cutting blade 2 dedicated for preliminary cutting may be located on the trajectory of the moved embedded block B. Then, the moving stage 12 is moved along the guide rail 11 to carry out preliminary cutting on the embedded block B for plural times using the cutting blade 2 dedicated for preliminary cutting. Upon completion of the preliminary cutting, the control unit 6 moves the holder 3 again and adjusts the position in such a manner that the cutting blade 2 dedicated for main sectioning should be located on the trajectory of the embedded block B. In this manner, the embedded block finished with preliminary cutting is subjected to main sectioning to manufacture the thin sections M.

Because the cutting blade 2 once used for sectioning can be reused as a cutting blade 2 for preliminary cutting in this manner, the cutting blades 2 can be exchanged while using them effectively instead of wasting. Thus, the running cost can be suppressed.

In addition, the exchanged cutting blade 2 is conveyed out from the mounting plane 20a of the holder 3 and disposed by a recollecting mechanism not shown. In this case, because a groove part 21b is formed on the upper side plate 21 of the holder 3, the recollecting mechanism may be incorporated inside the penetrating hole 2b provided to the cutting blade 2 via the groove part 21b, so as to recollect the cutting blades 2.

As described in the foregoing, the automatic thin-section manufacturing system 1 according to the present embodiment enables manufacturing of thin sections M by thinly cutting the embedded block B while automatically exchanging the cutting blades 2 already set at a predetermined rake angle θ. Thus, the burden of the operators can be minimized by eliminating the cutting blade 2 exchange operation which had been a burden to the operators. Furthermore, high quality thin sections M can be manufactured because sharp-edged cutting blades 2 are provided constantly for sectioning. Moreover, thin sections M of the same quality can be continuously manufactured because the cutting blade 2 can be exchanged while maintaining the cutting edge 2a at the same amount of protrusion.

The technical scope of the present invention is not only limited to those described in the embodiments above, and various types of modifications can be made so long as they do not deviate from the aim and scope of the invention.

For instance, in the embodiment above, plural magnets 25 were used to adsorb the cutting blade 2, but a single band-like magnet may be provided along the mounting plane 20a and the conveyor plane 41a. Again in this case, similar functional effects can be obtained. Furthermore, magnetic force effected by the magnet 25 was used to adsorb the cutting blade 2, however, this constitution is not only limited to a magnet 25. For instance, plural suction nozzles may constitute an adsorptive unit (member) to adsorb the cutting blade 2 by suction force. However, the automatic thin-section manufacturing system 1 of the present embodiment is preferred because a low cost component such as a magnet 25 can realize the adsorptive unit (member), which contributes in constructing a simplified and reduced cost constitution.

Furthermore, a conveyor unit 4 comprising a storage case 30, a conveyor path 40, and a conveyor mechanism 50 was used to convey the cutting blade 2 to the holder 3, however, for instance, there may be employed a multi-joint type hand robot capable of clamping and freely conveying the cutting blade 2, such that the cutting blade 2 may be delivered one by one from the conveyor unit to the mounting plane 20a provided on the holder 3. However, by employing the constitution according the present embodiment, the cutting blade 2 set already at the rake angle θ may be conveyed onto the holder 3, so as to make a smooth delivery and receipt of the cutting blade 2. In particular, because the cutting blade 2 can be surely delivered onto the mounting plane 20a of the holder 3 via the conveyor path 40, the holder 3 can be freely located independent of the position of the storage case 30; for instance, it can be allocated at a position as near as possible to the embedded block B. Thus, it allows a design of greater freedom.

What is claimed is:

1. An automatic thin-section manufacturing system for producing thin sections of a biological sample embedded in a block, the system comprising:
    a plurality of cutting blades each having a cutting edge on one end;
    a holder disposed at a rake angle relative to a surface of a block having a biological sample embedded therein;
    a transport unit including a vertical axis stage coupled to a moving stage and a cassette supporting the block, wherein the transport unit positions the block within the manufacturing system in spaced relationship to the holder;
    a mounting plane at the front end of the holder on which the plurality of cutting blades are mounted and aligned with their cutting edges exposed to an outer side of the mounting plane;
    an adsorptive member positioned on the mounting plane, which maintains the posture of the cutting blades by adsorbing a base end side of the cutting blades;
    a first pressing member arranged in the holder applying a clamping force to a cutting blade among the plurality of cutting blades, the cutting blade arranged in a predetermined position against the mounting plane, such that the cutting edge is in a first cutting position on the mounting plane;
    a second pressing member arranged in the holder adjacent to the first pressing member and positioned to receive the cutting blade from the first pressing member, the second pressing member applying a clamping force to the cutting blade on the mounting plane so that the cutting edge is in a second cutting position on the mounting plane;
    a conveyor unit including structure that slides out the cutting blades, by sequentially conveying the cutting blades to feed the cutting blades one by one on the mounting plane,
    wherein the transport unit moves the block relative to the first and second cutting positions on the mounting plane, such that the cutting blade cuts out a thin section of the biological sample from the block; and a control unit that exchanges the cutting blade by operating the conveyor unit to slide for respectively mounting a new cutting blade on the first cutting position and a reuse cutting blade on the second cutting position, and a second pressing member wherein the second pressing member is configured to hold the reuse cutting blade on the mounting plane so that the control unit can direct the transport unit to reuse the reuse cutting blade for preliminary cutting, and direct the transport unit to cut the thin section using the new cutting blade held by the first pressing member after preliminarily cutting the block with the reuse cutting blade.

2. The system as claimed in claim 1, wherein the adsorptive member comprises a plurality of magnets, and the base end side of the cutting blade is adsorbed by a magnetic force.

3. The system as claimed in claim 1, wherein the conveyor unit further comprises:

a storage case for storing the plurality of cutting blades;

a conveyor path located between the storage case and the holder and having a conveyor plane tilted at the rake angle, such that the cutting blades are aligned and transported by adjusting the conveyor plane at a same flat level with the mounting plane; and a conveyor mechanism that takes out the cutting blades one by one from the storage case, temporarily mounts a removed cutting blade on the conveyor plane, and conveys the removed cutting blade along the conveyor plane to feed it on the mounting plane;

wherein the adsorptive member is positioned along the conveyor plane, such that the adsorptive member adsorbs the base end side of the removed cutting blade to maintain the posture of the removed cutting blade.

4. The system as claimed in claim 1, wherein the control unit is configured to move the holder and adjust the holder position so that the cutting blade is located on a trajectory of the biological sample embedded in the block.

5. The system as claimed in claim 1 further comprising an upper side member superposed on the mounting plane on a same side as the first pressing member, the upper side member having a lower plane facing the mounting plane, and provided at a front end at an interval larger than the thickness of the cutting blade, such that the lower plane of the upper side member and the mounting plane guide the new cutting blade for accurately contacting a side of the reuse cutting blade.

* * * * *